(12) United States Patent
Forsberg et al.

(10) Patent No.: US 7,652,192 B2
(45) Date of Patent: Jan. 26, 2010

(54) CLONING OF TRANSGENIC UNGLULATES COMPRISING ARTIFICIAL CHROMOSOMES

(75) Inventors: Erik J. Forsberg, Oregon, WI (US); Kelly S. Mallon, Rio, WI (US); Paul J. Golueke, Poynette, WI (US); Michael D. Bishop, Rio, WI (US)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 471 days.

(21) Appl. No.: 10/468,951

(22) PCT Filed: Feb. 21, 2002

(86) PCT No.: PCT/US02/05476

§ 371 (c)(1),
(2), (4) Date: Jun. 24, 2004

(87) PCT Pub. No.: WO02/067665

PCT Pub. Date: Sep. 6, 2002

(65) Prior Publication Data

US 2006/0294603 A1    Dec. 28, 2006

Related U.S. Application Data

(60) Provisional application No. 60/271,200, filed on Feb. 23, 2001.

(51) Int. Cl.
C12N 15/00 (2006.01)
A01K 67/027 (2006.01)

(52) U.S. Cl. .............................. 800/24; 800/14; 800/15; 800/16; 800/17; 800/8

(58) Field of Classification Search .............. 800/15–27
See application file for complete search history.

(56) References Cited

U.S. PATENT DOCUMENTS

| 6,011,197 | A | | 1/2000 | Strelchenko et al. |
| 6,025,155 | A | * | 2/2000 | Hadlaczky et al. ......... 435/69.1 |
| 6,133,503 | A | | 10/2000 | Scheffler |

FOREIGN PATENT DOCUMENTS

| EP | 1395111 A2 | | 3/2004 |
| EP | 1611785 A1 | | 1/2006 |
| WO | WO 99/53751 | * | 10/1999 |
| WO | WO 02/067665 A2 | | 9/2002 |

OTHER PUBLICATIONS www.answers.com/transgenic.*
www.answers.com/topic/mosaicism.*
Vos. Mammalian Artificial Chromosomes as Tools for Gene Therapy. Current Opinions in Genetics and Development. 1998, vol. 8, pp. 351-359.*
Wilmut et al. Viable Offspring Derived from Fetal and Adult Mammalian Cells. Nature. Feb. 27, 1997, vol. 385, pp. 810-813.*
Baguisi et al., "Production of goats by somatic cell nuclear transfer." Nature Biotechnology, 17:456-461, 1999.
Co et al., "Generation of transgenic mice and germline transmission of a mammalian artificial chromosome introduced into embryos by pronuclear microinjection." Chromosome Research, 8:183-191, 2000.
Eyestone and Campbell, "Nuclear transfer from somatic cells: applications in farm animal species." Journal of Reproduction and Fertility, 489-497, 1999.
Grimes and Cooke, "Engineering mammalian chromosomes." Human Molecular Genetics, 7:1635-1640, 1998.
Langford et al., "Production of pigs transgenic for human regulators of complement activation using YAC technology." Transplantation Proceedings, 28: 862-863, 1996.
Niemann and Kues, "Transgenic livestock: premises and promises." Animal Reproduction Science 60-61: 277-293, 2000.
Prather et al., "Development of the techniques for nuclear transfer in pigs." Theriogenology, 51:487-498, 1999.
Zuelke, "Transgenic modification of cows milk for value-added processing." Reprod. Fertil. Dev., 10:671-676, 1998.

* cited by examiner

*Primary Examiner*—Deborah Crouch
(74) *Attorney, Agent, or Firm*—Clark & Elbing LLP; Karen L. Elbing

(57) ABSTRACT

The invention is directed in part to totipotent cells that have one or more artificial chromosomes; processes for producing such cells; processes for using such cells (e.g., nuclear transfer); transgenic embryos and transgenic animals cloned from such cells; and processes for producing such embryos and animals.

25 Claims, No Drawings

CLONING OF TRANSGENIC UNGLULATES COMPRISING ARTIFICIAL CHROMOSOMES

INTRODUCTION

The invention relates in part to the cloning of animals that comprise heterologous DNA molecules. Such transgenic animals preferably contain at least about 100 kilobase pairs of exogenous DNA in structures known to the skilled artisan as "artificial chromosomes."

BACKGROUND OF THE INVENTION

The following discussion of the background of the invention is merely provided to aid the reader in understanding the invention and is not admitted to describe or constitute prior art to the present invention.

Researchers have been developing methods for cloning mammalian animals over the past two decades. These reported methods typically include the steps of (1) isolating a pluripotent or totipotent cell; (2) inserting the cell or nucleus isolated from the cell into an enucleated oocyte (i.e., the oocyte's nucleus was previously extracted), and (3) allowing the embryo to mature in vivo.

The first successful nuclear transfer experiment using mammalian cells was reported in 1983, when pronuclei isolated from a murine (mouse) zygote were inserted into an enucleated oocyte and resulted in like offspring(s). See, e.g., McGrath & Solter, 1983, *Science* 220:1300-1302. Subsequently, other workers described the production of chimeric murine embryos (e.g., embryos that contain a subset of cells having significantly different nuclear DNA from other cells in the embryo) using murine primordial germ cells (PGCs). These cells are and can give rise to pluripotent cells (e.g., cells that can differentiate into other types of cells, and which may, but are not required to, differentiate into a grown animal). See, e.g., Matsui et al., 1992, *Cell* 70:841-847 and Resnick et al., 1992, *Nature* 359:550; Kato et al., 1994, *Journal of Reproduction and Fertility* Abstract Series, Society For the Study of Fertility, Annual Conference, Southampton, 13:38.

Progress has also been reported in the field of cloning ovine (sheep) animals (see, e.g., Willadsen, 1986, *Nature* 320:63-65; Campbell et al., 1996, *Nature* 380:64-66; PCT Publication WO 95/20042; Wilmut et al., 1997, *Nature* 385:810-813; PCT Publication WO 96/07732; PCT Publication WO 97/07668; and PCT publication WO 97/07669; and McCreath et al., 2000, *Nature,* 405:1066-1069), and bovine animals, (see, e.g., U.S. Pat. Nos. 4,994,384 and 5,057,420; Sims & First, 1993, *Theriogenology* 39:313; Keefer et al., 1994, *Mol. Reprod. Dev.* 38:264-268; Delhaise et al., 1995, *Reprod. Fert. Develop.* 7:1217-1219; Lavoir 1994, *J. Reprod. Dev.* 37:413-424; Stice et al., 1996, *Biol. Reprod.* 54: 100-110; and PCT application WO 95/10599 entitled "Embryonic Stem Cell-Like Cells").

Researchers have also disclosed methods that resulted in cloned bovine animals (cattle). Bovines have been cloned using an embryonic cell derived from a 2-64 cell embryo as a nuclear donor. This bovine animal was reportedly cloned by utilizing nuclear transfer techniques set forth in U.S. Pat. Nos. 4,994,384 and 5,057,420. Others reported that cloned bovine embryos were formed where an inner cell mass cell of a blastocyst stage embryo was utilized as a nuclear donor in a nuclear transfer procedure (Sims & First, 1993, *Theriogenology* 39:313; Keefer et al., 1994, *Mol. Reprod. Dev.* 38:264-268; and U.S. Pat. No. 6,107,543); a PGC isolated from fetal tissue as a nuclear donor (Delhaise et al., 1995, *Reprod. Fert. Develop.* 7:1217-1219; Lavoir 1994, *J. Reprod. Dev.* 37:413-424; and PCT application WO 95/10599 entitled "Embryonic Stem Cell-Like Cells"); a proliferating somatic cell (U.S. Pat. No. 5,945,577); and a reprogrammed nonembryonic cell (U.S. Pat. No. 6,011,197)

Additionally, researchers have reported methods for obtaining cloned porcine animals and porcine chimeric animals, specifically, where a nuclear donor obtained from a 4-cell embryo is placed inside an enucleated zygote. See, e.g., Prather et al., 1989, *Biology of Reproduction* 41: 414-418; Piedrahita et al., 1998, *Biology of Reproduction* 58: 1321-1329; and WO 94/26884, "Embryonic Stem Cells for Making Chimeric and Transgenic Ungulates," Wheeler, published Nov. 24, 1994. Also, researchers have reported nuclear transfer experiments using porcine nuclear donors and porcine oocytes. See., e.g., Nagashima et al., 1997, *Mol. Reprod. Dev.* 48: 339-343; Nagashima et al., 1992, *J. Reprod. Dev.* 38: 73-78; Prather et al., 1989, *Biol. Reprod.* 41: 414-419; Prather et al., 1990, *Exp. Zool.* 255: 355-358; Saito et al., 1992, *Assis. Reprod. Tech. Andro.* 259: 257-266; Terlouw et al., 1992, *Theriogenology* 37: 309, Pokajaeva et al., *Nature* 407, 86-90 (2000); Onishi et al., *Science* 289 1188-1190 (2000); and Betthauser et al., *Nature Biotechnology* 18: 1055-1059 (2000).

Researchers have also developed methods for generating transgenic cells, which may be applicable to the production of transgenic animals. Although several viral vectors, non-viral vectors, and other delivery systems have been developed for establishing transgenic cells, many of these technologies are constrained by multiple limitations. Specifically, these limitations include (1) the size of inserted DNA is limited to approximately 10 kilobases (kb); (2) integration of the DNA of interest cannot be specifically targeted into the cell's nuclear DNA; and (3) expression of a recombinant product from the DNA of interest cannot be well controlled. See, e.g., Mitani et al., 1993, *Trends Biotech,* 11: 162-166; U.S. Pat. No. 5,633,067, "Method of Producing a Transgenic Bovine or Transgenic Bovine Embryo," DeBoer et al, issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos," all of which are incorporated by reference herein in their entirety, including all figures, drawings, and tables.

Artificial chromosome technology is not constrained by the above-defined limitations. Moreover, researchers have discovered that artificial chromosomes can be replicated de novo. See, e.g., Kereso et al., 1996, *Chromosome Research* 4: 226-239, Holló et al., 1996, *Chromosome Research* 4: 240-247, U.S. Pat. No. 6,025,155, and U.S. Pat. No. 6,077,697.

Each reference used to provide background information in this section is hereby incorporated by reference in its entirety, including ant tables, figures, and claims.

Despite progress towards cloning mammals and establishing transgenic cells, there remains a great need in the art for materials and methods that enhance the efficiency for cloning transgenic animals. In particular, there remains a great need in the art to provide pluripotent and totipotent transgenic cells that can be utilized as nuclear donors. Furthermore, there remains a long felt need in the art for providing cell lines that are karyotypically stable and transgenic, which can be utilized in processes for cloning transgenic animals.

SUMMARY OF THE INVENTION

The invention relates in part to transgenic, totipotent, mammalian cells comprising one or more large, heterologous DNA constructs of 100 kbp or more. Preferably, the large DNA construct(s) are artificial chromosomes. Mammalian cells containing the large heterologous DNA construct(s) may be used for producing transgenic embryos and transgenic animals cloned from such cells. The invention is also directed in part to processes for producing totipotent cells that comprise one or more large, heterologous DNA constructs; processes for utilizing such cells; and processes for producing transgenic embryos and transgenic animals cloned from such cells.

Thus, in a first aspect, the invention features a method for producing transgenic cells by inserting a large, heterologous DNA construct of 100 kbp or more into cells. Such cells may preferably be used as nuclear donor cells in methods to produce transgenic animals, most preferably ungulates.

Preferably, a large, heterologous DNA construct is at least 200 Kbp, at least 300 Kbp, at least 400 Kbp, at least 500 Kbp, at least 750 Kbp, at least 1 Mbp, at least 5 Mbp, at least 10 Mbp, at least 20 Mbp, at least 50 Mbp, at least 100 Mbp, at least 500 Mbp, or at least 1000 Mbp. Particularly useful are artificial chromosomes of between 100 Kbp and 500 Mbp; between 500 Kbp and 500 Mbp; and between 1 Mbp and 500 Mbp.

In certain embodiments, the large, heterologous DNA construct(s) of this aspect are artificial chromosomes. Advantages of using artificial chromosomes include: (1) target DNA greater than 10 kb can be inserted into cells; (2) the location of target DNA of interest can be controlled; (3) transgenic animals and embryos containing large foreign genes, or a large copy number of one or more foreign genes, in a majority of cells can be obtained; and (4) the expression levels of a recombinant product from the DNA of interest can be manipulated in vitro. Specifically, expression levels can be manipulated by controlling the copy number of target DNA and/or its regulation by promoters, enhancers, etc., in an artificial chromosome, as defined in greater detail hereafter.

The term "artificial chromosome" as used herein refers to nucleic acid molecules that are generated by the manipulation of DNA, contain a centromere, and are capable of stable, autonomous replication in cells. An artificial chromosome (1) can replicate with naturally occurring chromosomes in the nucleus of target cell; (2) can be large in size (ranging in size from 100 kilobase pairs (Kbp) to 1000 megabase pairs (Mbp) in length, or more); (3) typically comprises a centromere, origins of replication, and telomeres; and (4) can comprise neutral DNA. Neutral DNA does not encode products that significantly alter the functions of a cell in which the artificial chromosome is located. For example, neutral DNA may encode ribosomal RNA. It is not typical that increasing levels of ribosomal RNA significantly alters cell functions. Neutral DNA can also be referred to as "satellite DNA."

Preferably, an artificial chromosome is at least 200 Kbp, at least 300 Kbp, at least 400 Kbp, at least 500 Kbp, at least 750 Kbp, at least 1 Mbp, at least 5 Mbp, at least 10 Mbp, at least 20 Mbp, at least 50 Mbp, at least 100 Mbp, at least 500 Mbp, or at least 1000 Mbp. Particularly useful are artificial chromosomes of between 100 Kbp and 500 Mbp; between 500 Kbp and 500 Mbp; and between 1 Mbp and 500 Mbp.

Materials and methods for producing, identifying, and characterizing artificial chromosomes are well known in the art. See, e.g., Kereso et al., 1996, *Chromosome Research* 4: 226-239, Holló et al., 1996, *Chromosome Research* 4: 240-247, International publication nos. WO00/18941, WO98/08964, WO97/16533 and WO97/40183, and U.S. Pat. Nos. 5,721,118, 6,025,155, 6,077,697, and 6,133,503, each of which is incorporated herein by reference in its entirety including all figures, tables, and drawings. These publications also describe shuttle vectors useful for incorporating target DNA into artificial chromosomes. Artificial chromosomes can arise from a portion of a natural chromosome by manipulation. Artificial chromosomes can be detected in cells by using chromosome identification techniques well known in the art. An example of such a technique is chromosome karyotype analysis.

Mammalian artificial chromosomes (MACs) can be generated by cellular mediated chromosome assembly from transfected alphoid, telomeric and marker DNAs (Harrington J. J. et al. Nature Genetics, 15, 345-355, 1997; Ikeno, M. et al, Nature Biotechnology 16, 431-439, 1998; Henning, K. A. et al, PNAS USA 96, 592-597, 1999) and even from non-alphoid DNA (du Sart D, et al, Nature Genetics 16, 144-153, 1997).

Minichromosomes may be generated by fragmenting natural human chromosomes using telomere-directed breakage (Shen M H, et al, Human Molecular Genetics 6, 1375-1382, 1997; Shen M H et al, Current Biology 10, 31-34, 1999). It is possible to transfer human-murine minichromosome chimeras (Shen M H et al, Current Biology 10, 31-34, 1999), fragmented human minichromosomes Tomizuka K et al, Nature Genetics 16, 133-143, 1997; Tomizuka K et al, PNAS USA 97, 722-797, 2000), and human small accessory chromosomes (SACs; Vermeesch J R et al, Human Genetics 105, 611-618, 1999) via microcell-mediated chromosome transfer (MMCT) to recipient cells.

The term "target DNA" as used herein refers to DNA that is intended to be or has been incorporated into a large heterologous DNA construct, preferably an artificial chromosome. The term "heterologous" is defined below. Target DNA can encode multiple types of recombinant products, as defined hereafter, and may exist in multiple copies when introduced into an artificial chromosome. One advantage of artificial chromosome technology is that target DNA copy number can be controlled and monitored in an artificial chromosome in vitro before the artificial chromosome comprising the target DNA is introduced into a cell. In addition, depending on the promoter used, expression can also be monitored in vitro. This advantage is contrasted with many existing techniques for creating transgenic cells, which cause random insertion of target DNA into a cell nuclear DNA. Materials and methods for introducing target DNA into an artificial chromosome and materials and methods for introducing the resulting artificial chromosome into cells are defined hereafter.

The term "heterologous nucleic acid" refers to nucleic acids having (1) a nucleic acid sequence that differs from the nucleic acid sequences present in cell's naturally occurring nuclear DNA; (2) a subset of nucleic acid having a nucleotide sequence that is present in cell nuclear DNA, but that exists in different proportions in the heterologous nucleic acid than in cell nuclear DNA; (3) a nucleic acid sequence originating from a species other than the species from which cell nuclear DNA originates; and (4) a nucleic acid sequence that differs from the DNA sequences present in cell's naturally occurring mitochondrial DNA.

Artificial chromosomes, such as mammalian artificial chromosomes [MACs], can be generated and isolated by the methods described in the publications above. In particularly preferred embodiments, two types of artificial chromosomes are used, both of which function in cells as stable, functional chromsomes. One type, herein referred to as ACEs ("Artificial Chromosome Expression systems" based on satellite DNA) is a stable heterochromatic chromosome, and the other type is a de novo-formed minichromosomes based on amplification of euchromatin.

Artificial chromosomes, and, in particular the two preferred types discussed above, provide an extra-genomic locus for targeted integration of up to multi-megabase pair size DNA fragments that contain single or multiple genes, including multiple copies of a single gene operatively linked to one promoter or each copy or several copies linked to separate promoters. Thus, methods provided can be used to introduce genes via MACs into cells and tissues of ungulate mammals. The artificial chromosomes with integrated heterologous DNA may be used in methods of production of gene products, particularly products that require expression of multigenic biosynthetic pathways, and also are intended for delivery into the nuclei of cells, such as nuclear donor cells used in nuclear transfer procedures, for production of transgenic ungulate mammals.

Additionally, such artificial chromosomes provide extra-genomic specific integration sites for introduction of genes encoding proteins of interest and permit up to multi-megabase size DNA integration so that, for example, genes encoding an entire metabolic pathway, a very large gene such as the cystic fibrosis transmembrane conductance regulator gene (approximately 250 kb genomic DNA gene), or several genes, such as multiple genes encoding a series of antigens for preparation of a multivalent vaccine, can be stably introduced into a cell.

The artificial chromosomes described herein, including ACEs and euchromatin-based minichromosomes, can be generated by introducing heterologous DNA, preferably including DNA encoding one or multiple selectable marker(s), into cells, preferably a stable cell line, growing the cells under selective conditions, and identifying from among the resulting cell clones those that include chromosomes with more than one centromere, fragments thereof, and/or heterochromatic structures. Amplification that produces the additional centromere(s) occurs in cells that contain chromosomes in which heterologous DNA has integrated near the centromere in the pericentric region of the chromosome. Selected cells comprising intermediates in the formation of such artificial chromosomes can then be used to generate complete artificial chromosomes.

For example, continued culture of cells containing a formerly dicentric chromosome under conditions that destabilize chromosomes (such as BrdU treatment) and/or under selective conditions can yield ACEs. Similarly, artificial chromosomes can be generated by culturing cells with multicentric (typically dicentric) chromosomes under conditions whereby the chromosome breaks to form a minichromosome and a formerly dicentric chromosome.

Among the MACs provided herein can be ACEs, which are predominantly heterochromatic (i.e., contain more heterochromatin than euchromatin, and preferably contain about 70% heterochromatin), and can comprise repeating units of short satellite DNA, so that without insertion of heterologous or foreign DNA, the chromosomes preferably contain no genetic information. They can thus be used as "safe" vectors for delivery of DNA to mammalian hosts because they do not contain any potentially harmful genes. ACEs are generated, not from the minichromosome fragment as, for example, in U.S. Pat. No. 5,288,625 (which is incorporated herein by reference in its entirety including all figures, tables, and drawings), but from the fragment of the formerly dicentric chromosome. In addition, euchromatic minichromosomes can be generated. Methods for generating one type of MAC, the minichromosome, is described in U.S. Pat. No. 5,288,625 (which is incorporated herein by reference in its entirety including all figures, tables, and drawings), along with its use for the expression of heterologous DNA are provided.

In preferred embodiments, (1) the artificial chromosome is an ACEs comprising one or more markers; (2) a marker is an antibiotic resistance gene selected from the group consisting of neomycin resistance gene, hygromycin resistance gene, and puromycin resistance gene; (3) the artificial chromosome comprises a DNA sequence that encodes one or more recombinant products; (4) a recombinant product is a ribozyme; (5) a recombinant product is antisense RNA; (6) a recombinant product is a peptide; (7) a recombinant product is a polypeptide; (8) a recombinant product is a protein; (9) a recombinant product is an enzyme; (10) a recombinant product is expressed in a biological fluid; (11) a recombinant product is expressed in a tissue; (12) a recombinant product confers resistance to one or more parasites and/or diseases; (13) an artificial chromosome comprises one or more regulatory elements; (14) a regulatory element is a promoter element; (15) a promoter element is selected from the group consisting of milk protein promoter, urine protein promoter, blood protein promoter, tear duct protein promoter, synovial protein promoter, mandibular gland protein promoter, casein promoter, β-casein promoter, melanocortin promoter, milk serum protein promoter, α-lactalbumin promoter, whey acid protein promoter, uroplakin promoter, and α-actin promoter; (17) a regulatory element is a repressor element; (18) a regulatory element is an insulator element; and (19) a regulatory element is an enhancer element.

The term "marker" as used herein refers to any DNA sequence that distinguishes a cell comprising an artificial chromosome, or a precursor thereof, from a cell that does not comprise the artificial chromosome or precursor. For example, a marker can be used in the initial steps of generating ACEs, whereby the marker distinguishes a cell containing a foreign nucleic acid from a cell that does not contain the foreign nucleic acid. Multiple types of markers, such as genes encoding green fluorescent protein, antibiotic resistance, β-galactosidase, glutamine synthetase, thymidine kinase, cytosine deaminase, and dihydrofolate reductase are well known in the art. Preferred as markers are DNA sequences that encode a molecule which directly or indirectly inactivates a drug that retards the growth of cells not expressing such a molecule. Examples of these latter described markers are blasticidin-S, neomycin, hygromycin, and puromycin resistance genes. These examples are not meant to be limiting and the invention relates in part to any marker known in the art.

The term "ribozyme" as used herein refers to ribonucleic acid molecules that can cleave other RNA molecules in specific regions. Ribozymes can bind to discrete regions on a RNA molecule, and then specifically cleave a region within that binding region or adjacent to the binding region. Ribozyme techniques can thereby decrease the amount of polypeptide translated from formerly intact message RNA molecules. For specific descriptions of ribozymes, see U.S. Pat. No. 5,354,855, entitled "RNA Ribozyme which Cleaves Substrate RNA without Formation of a Covalent Bond," Cech et al., issued on Oct. 11, 1994, and U.S. Pat. No. 5,591,610, entitled "RNA Ribozyme Polymerases, Dephosphorylases, Restriction Endoribonucleases and Methods," Cech et al., issued on Jan. 7, 1997, both of which are incorporated by reference in their entireties including all figures, tables, and drawings.

The term "antisense RNA" as used herein refers to any RNA that binds to mRNA with enough affinity to decrease the amount of protein translated from the mRNA. The amount of protein translated from the mRNA is preferably decreased by more than 20%; more preferably decreased by more than 50%, 70%, and 80%; and most preferably decreased by more than 90%. Antisense RNA materials and methods are well known in the art.

The terms "biological fluid" and the term "tissue" as used herein refer to any fluid or tissue in or from a biological organism. The fluids may include, but are not limited to, tears, saliva, milk, urine, amniotic fluid, semen, plasma, oviductal fluid, and synovial fluid. The tissues may include, but are not limited to, lung, heart, blood, liver, muscle, brain, pancreas, skin, and others.

The term "confers resistance" as used herein refers to the ability of a recombinant product to completely abrogate or partially alleviate the symptoms of a disease or parasitic condition. Hence, if a disease is related to inflammation, for example, a recombinant product can confer resistance to that inflammation if the inflammation decreases upon expression of the recombinant product. A recombinant product may confer resistance or partially confer resistance to a disease or parasitic condition, for example, if the recombinant product is an antisense RNA molecule that specifically binds to an mRNA molecule encoding a polypeptide responsible for the inflammation.

In preferred embodiments, the DNA with the selectable marker that is introduced into cells to generate artificial chromosomes includes sequences that target it to the pericentric region of the chromosome. Integration of the DNA into existing chromosomes in the cells can induce amplification that results in generation of additional centromeres.

Transgenic Cells

Large heterologous nucleic acid constructs, such as artificial chromosomes, can then be introduced into cells to produce stable transformed cell lines and cells. Introduction is effected by any suitable method or combination of methods including, but not limited to microinjection, cell fusion, microcell fusion, electroporation, sonoporation, electrofusion, projectile bombardment, calcium phosphate precipitation, lipid-mediated transfer systems, ligand/receptor systems and other such methods well known to the skilled artisan. ACEs in particular can be readily isolated and used for gene delivery. These artificial chromosomes can also be used in gene product production systems, production of humanized genetically transformed animal organs, and, most preferably, the generation of transgenic ungulates.

In certain embodiments, the invention relates to transgenic, totipotent, mammalian cells comprising at least one artificial chromosome, but the invention relates in part to any number of artificial chromosomes in a totipotent mammalian cell. A totipotent mammalian cell preferably comprises ten or fewer artificial chromosomes; more preferably comprises six or fewer artificial chromosomes, four or fewer artificial chromosomes, or two or fewer artificial chromosomes; and most preferably comprises one artificial chromosome. If a totipotent mammalian cell of the invention comprises more than one artificial chromosome, the artificial chromosomes may be identical or may differ from one another.

The term "transgenic" as used herein in reference to cells refers to a cell that comprises heterologous nucleic acid, preferably deoxyribonucleic acid (DNA).

In preferred embodiments, a transgenic cell comprises one or more heterologous DNA sequences. In other preferred embodiments, a transgenic cell is a cell in which one or more endogenous genes have been deleted, duplicated, activated, or modified. In particularly preferred embodiments, a transgenic cell comprises both one or more heterologous DNA sequences, and one or more endogenous genes that have been deleted, duplicated, activated, or modified.

An artificial chromosome present in a transgenic cell can comprise heterologous DNA. Heterologous DNA can encode multiple types of recombinant products, as defined hereafter.

The term "transgene" as used herein refers to a single gene that is partially or entirely transgenic in origin. In certain embodiments, greater than 50% of the transgene consists of heterologous DNA. In preferred embodiments, greater than 75% of the transgene consists of heterologous DNA, greater than 80% of the transgene consists of heterologous DNA, greater than 90% of the transgene consists of heterologous DNA, greater than 95% of the transgene consists of heterologous DNA, greater than 98% of the transgene consists of heterologous DNA, and 100% of the transgene consists of heterologous DNA.

The term "different nucleic acid sequence" as used herein refers to nucleic acid sequences that are not substantially similar. The term "substantially similar" as used herein in reference to nucleic acid sequences refers to two nucleic acid sequences having preferably 80% or more nucleic acid identity, more preferably 90% or more nucleic acid identity or most preferably 95% or more nucleic acid identity. Nucleic acid identity is a property of nucleic acid sequences that measures their similarity or relationship when aligned by means known to one skilled in the art. Identity is measured by dividing the number of identical bases in the two sequences by the total number of bases and multiplying the product by 100. Thus, two copies of exactly the same sequence have 100% identity, while sequences that are less highly conserved and have deletions, additions, or replacements have a lower degree of identity. Those skilled in the art will recognize that several computer programs are available for determining sequence identity and similarity using standard parameters, for example Gapped BLAST or PSI-BLAST (Altschul, et al. (1997) Nucleic Acids Res. 25:3389-3402), BLAST (Altschul, et al. (1990) J. Mol. Biol. 215:403-410), and Smith-Waterman (Smith, et al. (1981) J. Mol. Biol. 147:195-197). Preferably, the default settings of these programs will be employed, but those skilled in the art recognize whether these settings need to be changed and know how to make the changes.

The term "substantially similar" as used herein in reference to amino acid sequences refers to two amino acid sequences having preferably 50% or more amino acid identity, more preferably 70% or more amino acid identity or most preferably 90% or more amino acid identity. Amino acid identity is a property of amino acid sequence that measures their similarity or relationship. Identity is measured by dividing the number of identical residues in the two sequences by the total number of residues and multiplying the product by 100. Thus, two copies of exactly the same sequence have 100% identity, while sequences that are less highly conserved and have deletions, additions, or replacements have a lower degree of identity.

"Similarity" in protein sequences is measured by dividing the number of identical residues plus the number of conservatively substituted residues (see Bowie, et al. Science, (1999) 247, 1306-1310, which is incorporated herein by reference in its entirety, including any drawings, figures, or tables) by the total number of residues and gaps and multiplying the product by 100. "Similarity" in nucleic acid sequences is measured by dividing the number of identical bases by the total number of residues and gaps and multiplying the product by 100.

The term "recombinant product" as used herein refers to the product produced from a target DNA sequence. A recombinant product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art. This list of products is for illustrative purposes only and the invention relates to other types of recombinant products.

In preferred embodiments, (1) the mammalian cell is an ungulate cell; (2) the ungulate is selected from the group consisting of bovids, ovids, cervids, suids, equids and camelids; (3) the ungulate is bovine; (4) the mammalian cell is a nonembryonic cell; (5) the mammalian cell is a fetal cell; and (6) the mammalian cell is an adult cell.

The term "mammalian" as used herein refers to any animal of the class Mammalia. Preferably, a mammalian cell or cell line is a placental, a monotreme and a marsupial. Most preferably, a mammalian cell or cell line is a canid, felid, murid, leporid, ursid, mustelid, ungulate, ovid, suid, equid, bovid, caprid, cervid, and a human or non-human primate. A mammalian cell or cell line can be isolated from any source of mammalian cells including, but not limited to, a mammalian embryo, a mammalian fetus, and a mammalian animal.

The term "canid" as used herein refers to any animal of the family Canidae. Preferably, a canid cell or cell line is isolated from a wolf, a jackal, a fox, and a domestic dog.

The term "felid" as used herein refers to any animal of the family Felidae. Preferably, a felid cell or cell line is isolated from a lion, a tiger, a leopard, a cheetah, a cougar, and a domestic cat.

The term "murid" as used herein refers to any animal of the family Muridae. Preferably, a murid cell or cell line is isolated from a mouse and a rat.

The term "leporid" as used herein refers to any animal of the family Leporidae. Preferably, a leporid cell or cell line is isolated from a rabbit.

The term "ursid" as used herein refers to any animal of the family Ursidae. Preferably, a ursid cell or cell line is isolated from a bear.

The term "mustelid" as used herein refers to any animal of the family Mustelidae. Preferably, a mustelid cell or cell line is isolated from a weasel, a ferret, an otter, a mink, and a skunk.

The term "primate" as used herein refers to any animal of the Primate order. Preferably, a primate cell or cell line is isolated from an ape, a monkey, a chimpanzee, and a lemur.

The term "ungulate" as used herein refers to any animal of the polyphyletic group formerly known as the taxon Ungulata. Preferably, an ungulate cell or cell line is isolated from a camel, a hippopotamus, a horse, a tapir, and an elephant. Most preferably, an ungulate cell or cell line is isolated from a sheep, a cow, a goat, and a pig. Especially preferred in the bovine species are *Bos taurus, Bos indicus*, and *Bos buffaloes* cows or bulls.

The term "ovid" as used herein refers to any animal of the family Ovidae. Preferably, an ovid cell or cell line is isolated from a sheep.

The term "suid" as used herein refers to any animal of the family Suidae. Preferably, a suid cell or cell line is isolated from a pig or a boar.

The term "equid" as used herein refers to any animal of the family Equidae. Preferably, an equid cell or cell line is isolated from a zebra or an ass. Most preferably, an equid cell or cell line is isolated from a horse.

The term "bovid" as used herein refers to any animal of the family Bovidae. Preferably, an bovid cell or cell line is isolated from an antelope, an oxen, a cow, and a bison.

The term "caprid" as used herein refers to any animal of the family Caprinae. Preferably, a caprid cell or cell line is isolated from a goat.

The term "cervid" as used herein refers to any animal of the family Cervidae. Preferably, a cervid cell or cell line is isolated from a deer.

The term "immortalized" or "permanent" as used herein in reference to cells refers to cells that have exceeded the Hayflick limit. The Hayflick limit can be defined as the number of cell divisions that occur before a cell line becomes senescent. Hayflick set this limit to approximately 60 divisions for most non-immortalized cells. See, e.g., Hayflick and Moorhead, 1961, *Exp. Cell. Res.* 25: 585-621; and Hayflick, 1965, *Exp. Cell Research* 37: 614-636, incorporated herein by reference in their entireties including all figures, tables, and drawings. Therefore, an immortalized cell line can be distinguished from non-immortalized cell lines if the cells in the cell line are able to undergo more than 60 divisions. If the cells of a cell line are able to undergo more than 60 cell divisions, the cell line is an immortalized or permanent cell line. The immortalized cells of the invention are preferably able to undergo more than 70 divisions, are more preferably able to undergo more than 80 divisions, and are most preferably able to undergo more than 90 cell divisions.

The terms "primary culture" and "primary cell" refer to cells taken from a tissue source, and their progeny, grown in culture before subdivision and transfer to a subculture.

The terms "plated" or "plating" as used herein in reference to cells refer to establishing cell cultures in vitro. For example, cells can be diluted in cell culture media and then added to a cell culture plate or cell culture dish. Cell culture plates are commonly known to a person of ordinary skill in the art. Cells may be plated at a variety of concentrations and/or cell densities. In preferred embodiments, plated cells may grow to confluence.

The meaning of the term "cell plating" can also extend to the term "cell passaging." Cells of the invention can be passaged using cell culture techniques well known to those skilled in the art. The term "cell passaging" refers to such techniques which typically involve the steps of (1) releasing cells from a solid support and disassociation of these cells, and (2) diluting the cells in fresh media suitable for cell proliferation. Immortalized cells can be successfully grown by plating the cells in conditions where they lack cell to cell contact. Cell passaging may also refer to removing a portion of liquid medium bathing cultured cells and adding liquid medium from another source to the cell culture to dilute the cell concentration.

The term "proliferation" as used herein in reference to cells refers to a group of cells that can increase in size and/or can increase in numbers over a period of time.

The term "confluence" as used herein refers to a group of cells where a large percentage of the cells are physically contacted with at least one other cell in that group. Confluence may also be defined as a group of cells that grow to a maximum cell density in the conditions provided. For example, if a group of cells can proliferate in a monolayer and they are placed in a culture vessel in a suitable growth medium, they are confluent when the monolayer has spread across a significant surface area of the culture vessel. The surface area covered by the cells preferably represents about 50% of the total surface area, more preferably represents about 70% of the total surface area, and most preferably represents about 90% of the total surface area.

The cells and cell lines of the instant invention may be cultured. The term "cultured" as used herein in reference to cells refers to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in *Culture of Animal Cells: a manual of basic*

*techniques* (3$^{rd}$ edition), 1994, R. I. Freshney (ed.), Wiley-Liss, Inc.; *Cells: a laboratory manual* (vol. 1), 1998; D. L. Spector, R. D. Goldman, L. A. Leinwand (eds.), Cold Spring Harbor Laboratory Press; and *Animal Cells: culture and media*, 1994, D. C. Darling, S. J. Morgan John Wiley and Sons, Ltd., each of which is incorporated herein by reference in its entirety including all figures, tables, and drawings. Cells may be cultured in suspension and/or in monolayers with one or more substantially similar cells. Cells may be cultured in suspension and/or in monolayers with a heterogeneous population of cells. The term "heterogeneous" as utilized in the previous sentence can relate to any cell characteristics, such as cell type and cell cycle stage, for example. Cells may be cultured in suspension, cultured as monolayers attached to a solid support, and/or cultured on a layer of feeder cells, for example. The term "feeder cells" is defined hereafter. Furthermore, cells may be successfully cultured by plating the cells in conditions where they lack cell to cell contact. Preferably, cultured cells undergo cell division and are cultured for at least 5 days, more preferably for at least 10 days or 20 days, and most preferably for at least 30 days. Preferably, a significant number of cultured cells do not terminate while in culture. The terms "terminate" and "significant number" are defined hereafter. Nearly any type of cell can be placed in cell culture conditions. Cultured cells can be utilized to establish a cell line.

In particularly preferred embodiments, a cell may be "clonally propagated." In these embodiments, cells are diluted to an extent such that, statistically, some or all of the culture vessels into which the diluted cells are placed will contain only a single cell. Thus, the culture that grows within these culture vessels will be derived from a single cell. Materials and methods for clonally propagating cells are described in U.S. patent application Ser. No. 09/753,323, which is hereby incorporated in its entirety.

The term "terminating" and "terminate" as used herein with regard to cultured cells may refer to cells that undergo cell death, which can be measured using multiple techniques known to those skilled in the art (e.g., CytoTox96® Cytotoxicity Assay, Promega, Inc. catalog no. G1780; Celltiter96® Aqueous Cell Proliferation Assay Kit, Promega, Inc. catalog no. G3580; and Trypan Blue solution for cytotoxicity assays, Sigma catalog no. T6146). Termination may also be a result of apoptosis, which can be measured using multiple techniques known to persons skilled in the art (e.g., Dead End™ Apoptosis Detection Kit, Promega, Inc. catalog no. G7130). Terminated cells may be identified as those that have undergone cell death and/or apoptosis and have released from a solid surface in culture. In addition, terminated cells may lack intact membranes which can be identified by procedures described above. Also, terminated cells may exhibit decreased metabolic activity, which may be caused in part by decreased mitochondrial activity that can be identified by rhodamine 1,2,3, for example. Furthermore, termination can be refer to cell cultures where a significant number of cultured cells terminate. The term "significant number" in the preceding sentence refers to about 80% of the cells in culture, preferably about 90% of the cells in culture, more preferably about 100% of the cells in culture, and most preferably 100% of the cells in culture.

The term "suspension" as used herein refers to cell culture conditions in which the cells are not attached to a solid support. Cells proliferating in suspension can be stirred while proliferating using apparatus well known to those skilled in the art.

The term "monolayer" as used herein refers to cells that are attached to a solid support while proliferating in suitable culture conditions. A small portion of the cells proliferating in the monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "substantially similar" as used herein in reference to mammalian cells refers to cells from the same organism and the same tissue. Substantially similar can also refer to cell populations that have not significantly differentiated. For example, preferably less than 15% of the cells in a population of cells have differentiated, more preferably less than 10% of the cell population have differentiated, and most preferably less than 5% of the cell population have differentiated.

The term "cell line" as used herein refers to cultured cells that can be passaged one or more times. The invention preferably relates to cell lines that can be passaged more than 2, 5, 10, 15, 20, 30, 50, 80, 100, and 200 times. The concept of cell passaging is defined previously.

In preferred embodiments, (1) the mammalian cell is subject to manipulation; (2) the manipulation comprises the step of nuclear transfer; (3) the nuclear transfer comprises the step of inserting the totipotent mammalian cell into a recipient oocyte; (4) the manipulation comprises a step of cryopreservation of the mammalian cell; (5) the manipulation comprises a step of thawing of the mammalian cell; (6) the manipulation comprises a step of culturing the mammalian cell; (7) the manipulation comprises a step of passaging the mammalian cell; (8) the manipulation comprises a step of synchronizing the mammalian cell; (9) the manipulation comprises a step of introducing the mammalian cell to feeder cells; and (10) the manipulation comprises a step of dissociating the mammalian cell from other cells.

The term "manipulation" as used herein refers to the common usage of the term, which is the management or handling directed towards some object. Examples of manipulations are described herein.

The term "thawing" as used herein refers to the process of increasing the temperature of a cryopreserved cell, embryo, or portions of animals. Methods of thawing cryopreserved materials such that they are active after the thawing process are well-known to those of ordinary skill in the art.

The term "dissociating" as used herein refers to the materials and methods useful for pulling a cell away from another cell. For example, a blastomere (i.e., a cellular member of a morula or blastocyst stage embryo) can be pulled away from the rest of the developing cell mass by techniques and apparatus well known to a person of ordinary skill in the art. See, e.g., U.S. Pat. No. 4,994,384, entitled "Multiplying Bovine Embryos," issued on Feb. 19, 1991, hereby incorporated herein by reference in its entirety, including all figures, tables, and drawings. Alternatively, cells proliferating in culture can be separated from one another to facilitate such processes as cell passaging, which is described previously. In addition, dissociation of a cultured cell from a group of cultured cells can be useful as a first step in the process of nuclear transfer, as described hereafter. When a cell is dissociated from an embryo, the dissociation manipulation can be useful for such processes as re-cloning, a process described herein, as well as a step for multiplying the number of embryos.

The term "non-embryonic cell" as used herein refers to a cell that is not isolated from an embryo. Non-embryonic cells can be differentiated or non-differentiated. Non-embryonic cells refers to nearly any somatic cell, such as cells isolated from an ex utero animal. These examples are not meant to be limiting.

The term "fetus" as used herein refers to a developing cell mass that has implanted into the uterine membrane of a maternal host. A fetus can include such defining features as a genital ridge, for example. A genital ridge is a feature easily identified by a person of ordinary skill in the art, and is a recognizable feature in fetuses of most animal species. The term "fetal cell" as used herein refers to any cell isolated from and/or has arisen from a fetus or derived from a fetus. The term "non-fetal cell" is a cell that is not derived or isolated from a fetus.

When cells are isolated from a fetus, such cells are preferably isolated from fetuses where the fetus is between 20 days and parturition, between 30 days and 100 days, more preferably between 35 days and 70 days and between 40 days and 60 days, and most preferably about a 55 day fetus. An age of a fetus can be determined from the time that an embryo, which develops into the fetus, is established. The term "about" with respect to fetuses refers to plus or minus five days.

The term "parturition" as used herein refers to a time that a fetus is delivered from female recipient. A fetus can be delivered from a female recipient by abortion, c-section, or birth.

In preferred embodiments, the cells and cell lines of the instant invention are primary cells, embryonic cells, non-embryonic cells, fetal cells, genital ridge cells, primordial germ cells, embryonic germ cells, embryonic stem cells, somatic cells, adult cells, fibroblasts, differentiated cells, undifferentiated cells, amniotic cells, ovarian follicular cells, and cumulus cells. Preferably, such cells grow to confluent monolayers in culture.

The term "primordial germ cell" as used herein refers to a diploid somatic cell capable of becoming a germ cell. Primordial germ cells can be isolated from the genital ridge of a developing cell mass. The genital ridge is a section of a developing cell mass that is well-known to a person of ordinary skill in the art. See, e.g., Strelchenko, 1996, *Theriogenology* 45: 130-141 and Lavoir 1994, *J. Reprod. Dev.* 37: 413-424. Such cells, when cultured, are referred to by the skilled artisan as "embryonic germ cells."

The term "embryonic stem cell" as used herein refers to pluripotent cells isolated from an embryo that are maintained in in vitro cell culture. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells are well known to a person of ordinary skill in the art. See, e.g., WO 97/37009, entitled "Cultured Inner Cell Mass Cell-Lines Derived from Ungulate Embryos," Stice & Golueke, published Oct. 9, 1997, and Yang & Anderson, 1992, *Theriogenology* 38: 315-335, both of which are incorporated herein by reference in their entireties, including all figures, tables, and drawings.

The term "differentiated cell" as used herein refers to a cell that has developed from an unspecialized phenotype to that of a specialized phenotype. For example, embryonic cells can differentiate into an epithelial cell lining the intestine. It is highly unlikely that differentiated cells revert into their precursor cells in vivo or in vitro. However, materials and methods of the invention can reprogram differentiated cells into immortalized, totipotent cells. Differentiated cells can be isolated from a fetus or a live born animal, for example.

The term "undifferentiated cell" as used herein refers to a cell that has an unspecialized phenotype and is capable of differentiating. An example of an undifferentiated cell is a stem cell.

The term "asynchronous population" as used herein refers to cells that are not arrested at any one stage of the cell cycle. Many cells can progress through the cell cycle and do not arrest at any one stage, while some cells can become arrested at one stage of the cell cycle for a period of time. Some known stages of the cell cycle are $G_0$, $G_1$, S, $G_2$, and M. An asynchronous population of cells is not manipulated to synchronize into any one or predominantly into any one of these phases. Cells can be arrested in the $G_0$ stage of the cell cycle, for example, by utilizing multiple techniques known in the art, such as by serum deprivation. Examples of methods for arresting non-immortalized cells in one part of the cell cycle are discussed in WO 97/07669, entitled "Quiescent Cell Populations for Nuclear Transfer," hereby incorporated herein by reference in its entirety, including all figures, tables, and drawings.

The terms "synchronous population" and "synchronizing" as used herein refer to a fraction of cells in a population that are arrested (i.e., the cells are not dividing) in a discrete stage of the cell cycle. Preferably, about 50% of the cells in a population of cells are arrested in one stage of the cell cycle, more preferably about 70% of the cells in a population of cells are arrested in one stage of the cell cycle, and most preferably about 90% of the cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques well known to a person of ordinary skill in the art. Alternatively, cells can be distinguished by size utilizing techniques well known to a person of ordinary skill in the art, such as by the utilization of a light microscope and a micrometer, for example.

The term "adult cell" as used herein refers to a cell from a live-born animal.

The term "amniotic cell" as used herein refers to any cultured or non-cultured cell isolated from amniotic fluid. Examples of methods for isolating and culturing amniotic cells are discussed in Bellow et al., 1996, *Theriogenology* 45: 225; Garcia & Salaheddine, 1997, *Theriogenology* 47: 1003-1008; Leibo & Rail, 1990, *Theriogenology* 33: 531-552; and Vos et al., 1990, *Vet. Rec.* 127: 502-504, each of which is incorporated herein by reference in its entirety, including all figures tables and drawings. Particularly preferred are cultured amniotic cells that are rounded (e.g., cultured amniotic cells that do not display a fibroblast-like morphology). Also preferred amniotic cells are fetal fibroblast cells. The terms "fibroblast," "fibroblast-like," "fetal," and "fetal fibroblast" are defined hereafter.

The term "fibroblast" as used herein refers to cultured cells having a flattened and elongated morphology that are able to grow in monolayers. Preferably, fibroblasts grow to confluent monolayers in culture. While fibroblasts characteristically have a flattened appearance when cultured on culture media plates, fetal fibroblast cells can also have a spindle-like morphology. Fetal fibroblasts may require density limitation for growth, may generate type I collagen, and may have a finite life span in culture of approximately fifty generations. Preferably, fetal fibroblast cells rigidly maintain a diploid chromosomal content. For a description of fibroblast cells, see, e.g., *Culture of Animal Cells: a manual of basic techniques* ($3^{rd}$ edition), 1994, R. I. Freshney (ed), Wiley-Liss, Inc., incorporated herein by reference in its entirety, including all figures, tables, and drawings.

The term "uterine cell" as used herein refers to any cell isolated from a uterus. Preferably, a uterine cell is a cell deriving from a pregnant adult animal. In preferred embodiments, uterine cells are cells obtained from fluid that fills the uterine cavity. Such cells can be obtained by numerous methods well known in the art such as amniocentesis.

The term "ovarian follicular cell" as used herein refers to a cultured or non-cultured cell obtained from an ovarian follicle, other than an oocyte. Follicular cells may be isolated from ovarian follicles at any stage of development, including primordial follicles, primary follicles, secondary follicles, growing follicles, vesicular follicles, maturing follicles, mature follicles, and graafian follicles. Furthermore, follicular cells may be isolated when an oocyte in an ovarian follicle is immature (i.e., an oocyte that has not progressed to metaphase II) or when an oocyte in an ovarian follicle is mature (i.e., an oocyte that has progressed to metaphase II or a later stage of development). Preferred follicular cells include, but are not limited to, pregranulosa cells, granulosa cells, theca cells, columnar cells, stroma cells, theca interna cells, theca externa cells, mural granulosa cells, luteal cells, and corona radiata cells. Particularly preferred follicular cells are cumulus cells. Various types of follicular cells are known and can be readily distinguished by those skilled in the art. See, e.g., *Laboratory Production of Cattle Embryos*, 1994, Ian Gordon, CAB International; *Anatomy and Physiology of Farm Animals* (5th ed.), 1992, R. D. Frandson and T. L. Spurgeon, Lea & Febiger, each of which is incorporated herein by reference in its entirety including all figures, drawings, and tables. Individual types of follicular cells may be cultured separately, or a mixture of types may be cultured together.

The term "cumulus cell" as used herein refers to any cultured or non-cultured cell isolated from cells and/or tissue surrounding an oocyte. Persons skilled in the art can readily identify cumulus cells. Examples of methods for isolating and/or culturing cumulus cells are discussed in Damiani et al., 1996, *Mol. Reprod. Dev.* 45: 521-534; Long et al., 1994, *J: Reprod. Fert.* 102: 361-369; and Wakayama et al., 1998, *Nature* 394: 369-373, each of which is incorporated herein by reference in its entireties, including all figures, tables, and drawings. Cumulus cells may be isolated from ovarian follicles at any stage of development, including primordial follicles, primary follicles, secondary follicles, growing follicles, vesicular follicles, maturing follicles, mature follicles, and graafian follicles. Cumulus cells may be isolated from oocytes in a number of manners well known to a person of ordinary skill in the art. For example, cumulus cells can be separated from oocytes by pipeting the cumulus cell/oocyte complex through a small bore pipette, by exposure to hyaluronidase, or by mechanically disrupting (e.g. vortexing) the cumulus cell/oocyte complex. Additionally, exposure to $Ca^{++}/Mg^{++}$ free media can remove cumulus from immature oocytes. Also, cumulus cell cultures can be established by placing matured oocytes in cell culture media. Once cumulus cells are removed from media containing increased LH/FSH concentrations, they can to attach to the culture plate.

In a preferred embodiment, the culturing process can comprise the step of selecting totipotent mammalian cells comprising at least one artificial chromosome.

The term "selection" as used herein refers to a process for identifying cells that comprise a large heterologous nucleic acid construct, such as an artificial chromosome. Selection can be effected by identifying a marker region incorporated in an artificial chromosome. The term "marker" is defined previously. Preferably, from 50% to 100% of cells in cell cultures that have undergone selection comprise an artificial chromosome. In particularly preferred embodiments, greater than or equal to 50% of cells in cell cultures that have undergone selection comprise an artificial chromosome. More preferably, greater than or equal to 75% of cells in cell cultures that have undergone selection comprise an artificial chromosome. Most preferably, greater than or equal to 90% of cells in cell cultures that have undergone selection comprise an artificial chromosome.

The term "feeder cells" as used herein refers to cells grown in co-culture with target cells. Target cells can be precursor cells and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells, such as immortalized, totipotent cells may not require feeder cells for healthy growth. Feeder cells preferably grow in a mono-layer.

Feeder cells can be established from multiple cell types. Examples of these cell types are fetal cells, mouse cells, Buffalo rat liver cells, and oviductal cells. These examples are not meant to be limiting. Tissue samples can be broken down to establish a feeder cell line by methods well known in the art (e.g., by using a blender). Feeder cells may originate from the same or different animal species as the precursor cells. In an example of feeder cells established from fetal cells, ungulate fetuses and preferably bovine fetuses may be utilized to establish a feeder cell line where one or more cell types have been removed from the fetus (e.g., primordial germ cells, cells in the head region, and cells in the body cavity region). When an entire fetus is utilized to establish a fetal feeder cell line, feeder cells (e.g., fibroblast cells) and precursor cells (e.g., primordial germ cells) can arise from the same source (e.g., one fetus).

The term "drug" as used herein refers to any type of molecule that retards the normal growth rate of a cell. A normal cell growth rate is measured in the absence of drug. A drug may also lyse cells.

In another aspect, the invention features a method for producing transgenic ungulates by introducing a large heterologous nucleic acid construct into a nuclear donor cell, then fusing this nuclear donor cell into an enucleated recipient cell to form a nuclear transfer embryo, activating this embryo, and finally transferring this embryo into a maternal host to produce a transgenic animal. In particularly preferred embodiments, the transgenic animal is an ungulate.

Nuclear Transfer

Most preferably, transgenic animals are prepared by introducing a heterologous nucleic acid molecule, preferably an artificial chromosome, into a nuclear donor cell, then fusing this nuclear donor cell into an enucleated recipient cell, most preferably an enucleated oocyte, to form a nuclear transfer embryo, activating this embryo, and finally transferring this embryo into a maternal host to produce a transgenic animal.

In preferred embodiments, the artificial chromosome(s) is introduced into the cybrid by introduction into the nuclear donor cell prior to the fusion with the enucleated recipient cell or enucleated oocyte. In other preferred embodiments, the artificial chromosome(s) is introduced into the cybrid formed by fusion of the nuclear donor cell with the enucleated recipient cell or enucleated oocyte. In yet other preferred embodiments, the artificial chromosome(s) is introduced into the cybrid simultaneously with the fusion of the nuclear donor cell with the enucleated recipient cell or enucleated oocyte The terms "nuclear transfer" and "nuclear transfer procedure" as used herein refer to introducing a full complement of nuclear DNA from one cell to an enucleated cell. Nuclear transfer methods are well known to a person of ordinary skill in the art. See, U.S. Pat. No. 4,994,384 to Prather et al., entitled "Multiplying Bovine Embryos," issued on Feb. 19, 1991; U.S. Pat. No. 5,057,420 to Massey, entitled "Bovine Nuclear Transplantation," issued on Oct. 15, 1991; U.S. Pat. No. 5,994,619, issued on Nov. 30, 1999 to Stice et al., entitled "Production of Chimeric Bovine or Porcine Animals Using Cultured Inner Cell Mass Cells; U.K. Patents Nos. GB 2,318, 578 GB 2,331,751, issued on Jan. 19, 2000 to Campbell et al. and Wilmut et al., respectively, entitled "Quiescent Cell Populations For Nuclear Transfer"; U.S. Pat. No. 6,011,197 to Strelchenko et al., entitled "Method of Cloning Bovines Using Reprogrammed Non-Embryonic Bovine Cells," issued on Jan. 4, 2000; and in U.S. patent application Ser. No. 09/753,323 entitled "Method of Cloning Porcine Animals, each of which are hereby incorporated by reference in its entirety including all figures, tables and drawings. Nuclear transfer may be accomplished by using oocytes that are not surrounded by a zona pellucida.

In a nuclear transfer procedure, a nuclear donor cell, or the nucleus thereof, is introduced into a recipient cell. A recipient cell is preferably an oocyte and is preferably enucleated. However, the invention relates in part to nuclear transfer, where a nucleus of an oocyte is not physically extracted from the oocyte. It is possible to establish a nuclear transfer embryo where nuclear DNA from the donor cell is replicated during cellular divisions. See, e.g., Wagoner et al., 1996, "Functional enucleation of bovine oocytes: effects of centrifugation and ultraviolet light," Theriogenology 46: 279-284. In addition, nuclear transfer may be accomplished by combining one nuclear donor and more than one enucleated oocyte. Also, nuclear transfer may be accomplished by combining one nuclear donor, one or more enucleated oocytes, and the cytoplasm of one or more enucleated oocytes. The resulting combination of a nuclear donor cell and a recipient cell can be referred to variously as a "nuclear transfer embryo," a "hybrid cell," or a "cybrid."

Furthermore, a nuclear donor may arise from an animal of the same species from which a nuclear recipient is isolated. Alternatively, a nuclear donor may arise from an animal of a different specie from which a nuclear recipient is isolated. For example, a differentiated cell isolated from an ear punch of a water buffalo may be utilized as a nuclear donor and an oocyte isolated from a bovine animal may be utilized as a nuclear acceptor. Thus, xenospecific nuclear transfer is contemplated by the instant invention.

The term "nuclear donor" as used herein refers to any cell, or nucleus thereof, having nuclear DNA that can be translocated into an oocyte. A nuclear donor may be a nucleus that has been isolated from a cell. Multiple techniques are available to a person of ordinary skill in the art for isolating a nucleus from a cell and then utilizing the nucleus as a nuclear donor. See, e.g., U.S. Pat. Nos. 4,664,097, 6,011,197, and 6,107,543, each of which is hereby incorporated by reference in its entirety including all figures, tables and drawings. Any type of cell can serve as a nuclear donor. Examples of nuclear donor cells include, but are not limited to, cultured and non-cultured cells isolated from an embryo arising from the union of two gametes in vitro or in vivo; embryonic stem cells (ES cells) arising from cultured embryonic cells (e.g., pre-blastocyst cells and inner cell mass cells); cultured and non-cultured cells arising from inner cell mass cells isolated from embryos; cultured and non-cultured pre-blastocyst cells; cultured and non-cultured fetal cells; cultured and non-cultured adult cells; cultured and non-cultured primordial germ cells; cultured and non-cultured germ cells (e.g., embryonic germ cells); cultured and non-cultured somatic cells isolated from an animal; cultured and non-cultured cumulus cells; cultured and non-cultured amniotic cells; cultured and non-cultured fetal fibroblast cells; cultured and non-cultured genital ridge cells; cultured and non-cultured differentiated cells; cultured and non-cultured cells in a synchronous population; cultured and non-cultured cells in an asynchronous population; cultured and non-cultured serum-starved cells; cultured and non-cultured permanent cells; and cultured and non-cultured totipotent cells. See, e.g., Piedrahita et al., 1998, *Biol. Reprod.* 58: 1321-1329; Shim et al., 1997, *Biol. Reprod.* 57: 1089-1095; Tsung et al., 1995, *Shih Yen Sheng Wu Hsueh Pao* 28: 173-189; and Wheeler, 1994, *Reprod. Fertil. Dev.* 6: 563-568, each of which is incorporated herein by reference in its entirety including all figures, drawings, and tables. In addition, a nuclear donor may be a cell that was previously frozen or cryopreserved.

The term "activation" refers to any materials and methods useful for stimulating a cell to divide before, during, and after a nuclear transfer step. Cybrids may require stimulation in order to divide after a nuclear transfer has occurred. The invention pertains to any activation materials and methods known to a person of ordinary skill in the art. Although electrical pulses are sometimes sufficient for stimulating activation of cybrids, other means are sometimes useful or necessary for proper activation of the cybrid. Chemical materials and methods useful for activating embryos are described below in other preferred embodiments of the invention.

Examples of non-electrical means for activation include agents such as ethanol; inositol trisphosphate ($IP_3$); $Ca^{++}$ ionophores (e.g., ionomycin) and protein kinase inhibitors (e.g., 6-dimethylaminopurine (MAP)); temperature change; protein synthesis inhibitors (e.g., cyclohexamide); phorbol esters such as phorbol 12-myristate 13-acetate (PMA); mechanical techniques; and thapsigargin. The invention includes any activation techniques known in the art. See, e.g., U.S. Pat. No. 5,496,720, entitled "Parthenogenic Oocyte Activation" to Susko-Parrish et al., issued on Mar. 5, 1996; and U.S. Pat. No. 6,077,710, issued on Jun. 20, 2000, each of which is incorporated by reference herein in its entirety, including all figures, tables, and drawings.

The term "fusion" as used herein in reference to nuclear transfer refers to the combination of portions of lipid membranes corresponding to the nuclear donor and the recipient oocyte. Lipid membranes can correspond to the plasma membranes of cells or nuclear membranes, for example. The fusion can occur between the nuclear donor and recipient oocyte when they are placed adjacent to one another, or when the nuclear donor is placed in the perivitelline space of the recipient oocyte, for example. Specific examples for translocation of the totipotent mammalian cell into the oocyte are described hereafter in other preferred embodiments. These techniques for translocation are fully described in the references cited previously herein in reference to nuclear transfer.

The term "electrical pulses" as used herein refers to subjecting the nuclear donor and recipient oocyte to electric current. For nuclear transfer, the nuclear donor and recipient oocyte can be aligned between electrodes and subjected to electrical current. The electrical current can be alternating current or direct current. The electrical current can be delivered to cells for a variety of different times as one pulse or as multiple pulses. The cells are typically cultured in a suitable medium for the delivery of electrical pulses. Examples of electrical pulse conditions utilized for nuclear transfer are described in the references and patents previously cited herein in reference to nuclear transfer.

The term "fusion agent" as used herein in reference to nuclear transfer refers to any compound or biological organism that can increase the probability that portions of plasma membranes from different cells will fuse when a totipotent mammalian cell nuclear donor is placed adjacent to the recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

The term "suitable concentration" as used herein in reference to fusion agents, refers to any concentration of a fusion agent that affords a measurable amount of fusion. Fusion can be measured by multiple techniques well known to a person of ordinary skill in the art, such as by utilizing a light microscope, dyes, and fluorescent lipids, for example.

The term "totipotent" as used herein refers to a cell, embryo, or fetus capable of giving rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps. Totipotent cells, embryos, and fetuses may also be used to generate incomplete animals such as those useful for organ harvesting, e.g., having genetic modifications to eliminate growth of an organ or appendage by manipulation of a homeotic gene.

The term "live born" as used herein preferably refers to an animal that exists ex utero. A "live born" animal may be an animal that is alive for at least one second from the time it exits the maternal host. A "live born" animal may not require the circulatory system of an in utero environment for survival. A "live born" animal may be an ambulatory animal. Such animals can include pre- and post-pubertal animals. As discussed previously, a live born animal may lack a portion of what exists in a normal animal of its kind.

In preferred embodiments, (1) totipotent cells arise from at least one precursor cell; (2) a precursor cell is isolated from and/or arises from any region of a ungulate animal; (3) a precursor cell is isolated from and/or arises from any cell in culture; (4) a precursor cell is selected from the group consisting of a primary cell, a non-embryonic cell, a non-fetal cell, a differentiated cell, an undifferentiated cell, a somatic cell, an embryonic cell, a fetal cell, an embryonic stem cell, a primordial germ cell, a genital ridge cell, a cumulus cell, an amniotic cell, a fetal fibroblast cell, a uterine cell, an ovarian follicular cell, a cumulus cell, an hepatocyte, an embryonic germ cell, an adult cell, a cell isolated from an asynchronous population of cells, and a cell isolated from a synchronized population of cells where the synchronous population is not arrested in the $G_0$ stage of the cell cycle; (5) totipotent cells have a morphology of an embryonic germ cell.

The terms "precursor cell" or "precursor cells" as used herein refer to a cell or cells used to create a cell line of totipotent cells. Precursor cells can be isolated from, any animal, preferably from a mammal, and more preferably from an ungulate. The precursor cell or cells may be isolated from nearly any cellular entity. For example, a precursor cell or cells may be isolated from blastocysts, embryos, fetuses, and cell lines (e.g., cell lines established from embryonic cells), preferably isolated from fetuses and/or cell lines established from fetal cells, and more preferably isolated from ex utero animals and/or cell cultures and/or cell lines established from such ex utero animals. An ex utero animal may exist as a newborn animal, adolescent animal, yearling animal, and adult animal. The ex utero animals may be alive or post mortem. Examples of precursor cells include, but are not limited to, non-embryonic cells; non-fetal cells; differentiated cells; adult cells; somatic cells; embryonic cells; fetal cells; embryonic stem cells; primordial germ cells; genital ridge cells; uterine cells; amniotic cells; ovarian follicular cells; cumulus cells; cells isolated from an asynchronous population of cells; and cells isolated from a synchronized population of cells where the synchronous population is not arrested in the $G_0$ stage of the cell cycle; and any of the forgoing that are cultured, cultured as cell lines and/or totipotent.

The term "arises from" as used herein refers to the conversion of one or more cells into one or more cells having at least one differing characteristic. For example, (1) a non-totipotent precursor cell can be converted into a totipotent cell by utilizing features of the invention described hereafter; (2) a precursor cell can develop a cell morphology of an embryonic germ cell; (3) a precursor cell can give rise to a cultured cell; (4) a precursor cell can give rise to a cultured cell line; and (5) a precursor cell can give rise to a cultured permanent cell line. A conversion process can be referred to as a reprogramming step. In addition, the term "arises from" refers to establishing totipotent embryos from totipotent cells of the invention by using a nuclear transfer process, as described hereafter.

The terms "reprogramming" or "reprogrammed" as used herein refer to materials and methods that can convert a non-totipotent cell into a totipotent cell. Distinguishing features between totipotent and non-totipotent cells are described previously. An example of materials and methods for converting non-totipotent cells into totipotent cells is to incubate precursor cells with a receptor ligand cocktail. Receptor ligand cocktails are described hereafter. In preferred embodiments, culturing of a cell is a sufficient stimulus to render a cell totipotent.

The term "reprogramming" or "reprogrammed" as used herein can also refer to materials and methods that can convert a cell into another cell having at least one differing characteristic. Also, such materials and methods may reprogram or convert a cell into another cell type that is not typically expressed during the life cycle of the former cell. For example, (1) a non-totipotent cell can be reprogrammed into an totipotent cell; (2) a precursor cell can be reprogrammed into a cell having a morphology of an EG cell; and (3) a precursor cell can be reprogrammed into a totipotent cell. An example of materials and methods for converting a precursor cell into a totipotent cell having EG cell morphology is described hereafter.

The term "isolated" as used herein in reference to cells refers to a cell that is mechanically separated from another group of cells. Examples of a group of cells are a developing cell mass, a cell culture, a cell line, and an animal. These examples are not meant to be limiting and the invention relates to any group of cells. Methods for isolating one or more cells from another group of cells are well known in the art. See, e.g., *Culture of Animal Cells: a manual of basic techniques* ($3^{rd}$ edition), 1994, R. I. Freshney (ed.), Wiley-Liss, Inc.; *Cells:* a laboratory manual (vol. 1), 1998, D. L. Spector, R. D. Goldman, L. A. Leinwand (eds.), Cold Spring Harbor Laboratory Press; and *Animal Cells: culture and media*, 1994, D. C. Darling, S. J. Morgan, John Wiley and Sons, Ltd.

The terms "cryopreservation" or "cryopreserved" as used herein refer to freezing a cell, embryo, or animal of the invention. The cells, embryos, or portions of animals of the invention are frozen at temperatures lower than 0° C., preferably lower than −80° C., more preferably at temperatures lower than −140° C., and most preferably at temperatures lower than −196° C. Cells and embryos in the invention can be cryopreserved for an indefinite amount of time. It is known that biological materials can be cryopreserved for more than fifty years. For example, semen that is cryopreserved for more than fifty years can be utilized to artificially inseminate a female bovine animal. Methods and tools for cryopreservation are well-known to those skilled in the art. See, e.g., U.S. Pat. No. 5,160,312, entitled "Cryopreservation Process for Direct Transfer of Embryos," issued to Voelkel on Nov. 3, 1992, hereby incorporated by reference herein in its entirety, including all figures, tables, and drawings.

For the purposes of the present invention, the terms "embryo" or "embryonic" as used herein refer to a developing cell mass that has not implanted into the uterine membrane of a maternal host. Hence, the term "embryo" as used herein can refer to a fertilized oocyte, a cybrid (defined herein), a pre-blastocyst stage developing cell mass, and/or any other developing cell mass that is at a stage of development prior to implantation into the uterine membrane of a maternal host. Embryos of the invention may not display a genital ridge. Hence, an "embryonic cell" is isolated from and/or has arisen from an embryo.

An embryo can represent multiple stages of cell development. For example, a one cell embryo can be referred to as a zygote, a solid spherical mass of cells resulting from a cleaved embryo can be referred to as a morula, and an embryo having a blastocoel can be referred to as a blastocyst.

The terms "enucleated oocyte" or "enucleated recipient cell" as used herein refer to an oocyte which has had its nucleus removed. Typically, a needle can be placed into an oocyte and the nucleus can be aspirated into the inner space of the needle. The needle can be removed from the oocyte without rupturing the plasma membrane. This enucleation technique is well known to a person of ordinary skill in the art. See, U.S. Pat. No. 4,994,384; U.S. Pat. No. 5,057,420; and Willadsen, 1986, *Nature* 320:63-65. An enucleated oocyte can be prepared from a young or an aged oocyte. An enucleated oocyte is preferably prepared from an oocyte that has been matured, in vitro or in vivo, for some period of time. This time can vary, depending on the source species for the oocyte. For example, bovine oocytes are preferably matured for between 10 hours and 40 hours, more preferably for between 16 hours and 36 hours, and most preferably between 20 hours and 32 hours. In contrast, porcine oocytes are preferably matured for greater than 24 hours, and more preferably matured for greater than 36 hours. In particularly preferred embodiments, a porcine oocyte is matured for more than 40 hours, up to about 96 hours, more preferably from 42-54 hours, and even more preferably from 42 to 48 hours.

The terms "maturation" and "matured" as used herein refer to process in which an oocyte is incubated in a medium in vitro. Oocytes can be incubated with multiple media well known to a person of ordinary skill in the art. See, e.g., Saito et al., 1992, *Roux's Arch. Dev. Biol.* 201: 134-141 for bovine organisms and Wells et al., 1997, *Biol. Repr.* 57: 385-393 for ovine organisms and also Mattioli et al., 1989, *Theriogenology* 31: 1201-1207; Jolliff & Prather, 1997, *Biol. Reprod.* 56: 544-548; Funahashi & Day, 1993, *J. Reprod. Fert.* 98: 179-185; Nagashima et al., 1997, *Mol. Reprod. Dev.* 38: 339-343; Abeydeera et al., 1998, *Biol. Reprod.* 58: 213-218; Funahashi et al., 1997, *Biol. Reprod.* 57: 49-53; and Sawai et al., 1997, *Biol. Reprod.* 57: 1-6, each of which are incorporated herein by reference in their entireties including all figures, tables, and drawings. Maturation media can comprise multiple types of components, including microtubule inhibitors (e.g. cytochalasin B), hormones and growth factors. Other examples of components that can be incorporated into maturation media are discussed in WO 97/07668, entitled "Unactivated Oocytes as Cytoplast Recipients for Nuclear Transfer," Campbell & Wilmut, published on Mar. 6, 1997, hereby incorporated herein by reference in its entirety, including all figures, tables, and drawings. The time of maturation can be determined from the time that an oocyte is placed in a maturation medium to the time that the oocyte is subject to a manipulation (e.g., enucleation, nuclear transfer, fusion, and/or activation).

Oocytes can be matured for any period of time: an oocyte can be matured for greater than 10 hours, greater than 20 hours, greater than 24 hours, greater than 36 hours, greater than 48 hours, greater than 60 hours, greater than 72 hours, and greater than 90 hours. The term "about" with respect to oocyte maturation refers to plus or minus 3 hours.

An oocyte can also be matured in vivo. Time of maturation may be the time that an oocyte receives an appropriate stimulus to resume meiosis to the time that the oocyte is manipulated. Similar maturation periods described above for in vitro matured oocytes apply to in vivo matured oocytes.

Nuclear transfer may be accomplished by combining one nuclear donor and more than one enucleated oocyte. In addition, nuclear transfer may be accomplished by combining one nuclear donor, one or more enucleated oocytes, and the cytoplasm of one or more enucleated oocytes.

The term "young oocyte" as used herein refers to an oocyte that has been matured in vitro for a time less than or equal to the length of time between the onset of estrus and ovulation in vivo. For example, the onset of estrus is signaled by a surge in leutenizing hormone. A cow typically ovulates about 26 hours following the onset of estrus. Thus, a young oocyte is an oocyte matured for about 26 hours or less, preferably 16 to 17 hours. Methods for measuring the length of time between the onset of estrus and ovulation are well known to the skilled artisan. See, e.g., P. T. Cupps, "Reproduction in Domestic Animals," Fourth Edition, Academic Press, San Diego, Calif., USA, 1991. For horses, ovulation occurs about 33 hours after onset of estrus; for pigs, about 40 hours; for sheep and goats, about 24-36 hours; for dogs, about 40-50 hours; and for cats, about 24-36 hours. The term "young oocyte" may also refer to an oocyte that has been matured and ovulated in vivo and that is collected at about the time of ovulation. The term about in this context refers to +/−1 hour.

Oocytes can be isolated from live animals using methods well known to a person of ordinary skill in the art. See, e.g., Pieterse et al., 1988, "Aspiration of bovine oocytes during transvaginal ultrasound scanning of the ovaries," *Theriogenology* 30: 751-762. Oocytes can be isolated from ovaries or oviducts of deceased or live born animals. Suitable media for in vitro culture of oocytes are well known to a person of ordinary skill in the art. See, e.g., U.S. Pat. No. 5,057,420, which is incorporated by reference herein.

Some young oocytes can be identified by the appearance of their ooplasm. Because certain cellular material (e.g., lipids) have not yet dispersed within the ooplasm. Young oocytes can have a pycnotic appearance. A pycnotic appearance can be characterized as clumping of cytoplasmic material. For example, in bovines, a "pycnotic" appearance is to be contrasted with the appearance of oocytes that are older than 28 hours, which have a more homogenous appearing ooplasm.

The term "aged oocyte" as used herein refers to an oocyte that has been matured in vitro for a time greater than the length of time between the onset of estrus and ovulation in vivo. The term "aged oocyte" may also refer to an oocyte that has been matured and ovulated in vivo and that is collected later than about 1 hour after the time of ovulation. An aged oocyte can be identified by its characteristically homogenous ooplasm. This appearance is to be contrasted with the pycnotic appearance of young oocytes as described previously herein. The age of the oocyte can be defined by the time that has elapsed between the time that the oocyte is placed in a suitable maturation medium and the time that the oocyte is activated. The age of the oocyte can dramatically enhance the efficiency of nuclear transfer. For example, an aged oocyte can be more susceptible to activation stimuli than a young oocyte.

The term "ovulated in vivo" as used herein refers to an oocyte that is isolated from an animal a certain number of hours after the animal exhibits characteristics that it is in estrus. The characteristics of an animal in estrus are well known to a person of ordinary skill in the art, as described in references disclosed herein.

The terms "maternal recipient" and "recipient female" as used herein refer to a female animal which is implanted with an embryo for development of the embryo. A maternal recipient may be either homospecific or xenospecific to the implanted embryo. For example it has been shown in the art that bovine embryos can develop in the oviducts of sheep. Stice & Keefer, 1993, "Multiple generational bovine embryo cloning," *Biology of Reproduction* 48: 715-719. Implanting techniques are well known to a person of ordinary skill in the art. See, e.g., Polge & Day, 1982, "Embryo transplantation and preservation," *Control of Pig Reproduction*, D J A Cole and G R Foxcroft, eds., London, UK, Butterworths, pp. 227-291; Gordon, 1997, "Embryo transfer and associated techniques in pigs," *Controlled reproduction in pigs* (Gordon, ed), CAB International, Wallingford UK, pp 164-182; and Kojima, 1998, "Embryo transfer," *Manual of pig embryo transfer procedures*, National Livestock Breeding Center, Japanese Society for Development of Swine Technology, pp 76-79, each of which is incorporated herein by reference in its entirety, including all figures, tables, and drawings.

The term "replication unit" as used herein refers to that portion of a chromosome or other DNA molecule capable of being replicated that is copied from a given origin of replication. A chromosome in eukaryotes has many replication units. The term "origin of replication" refers to the location in a DNA molecule where its replication begins.

The term "essentially no homologous DNA" means that the DNA molecule in question comprises almost entirely heterologous DNA. Preferably, a molecule which contains essentially no homologous DNA comprises at least 98%, 99%, 99.5%, or 99.9% heterologous DNA when the number of base pairs of heterologous DNA in the molecule is divided by the overall number of base pairs in the molecule.

The term "homologous DNA" as used herein refers to DNA having the same nucleic acid sequence as DNA sequences present in cell nuclear DNA.

The term "germ line" refers to those cells which give rise to the reproductive cells of an organism. These cells contain the complete haploid genome of an organism and will pass these DNA molecules to the descendants of the organism in question.

The term "somatic cell" refers to those cells of an organism which are not involved in the production of gametes, e.g., they are not involved in passing the genome to the next generation of the organism in question.

Transgenic Embryos, Fetuses, and Animals

In yet another aspect, the instant invention relates in part to any embryos, fetuses, and animals emanating from totipotent mammalian cells of the invention, where one or more cells in these developing cell masses comprise at least one large heterologous nucleic acid construct, most preferably an artificial chromosome.

In preferred embodiments, at least 10%, 20%, 30%, 40%, 50%, 60%, 70%, 80%, or 90% of the cells of the embryos, fetuses, and animals emanating from totipotent mammalian cells of the invention comprise at least one large heterologous nucleic acid construct. Most preferably, between 90% and all of the cells of the embryos, fetuses, and animals emanating from totipotent mammalian cells of the invention comprise at least one large heterologous nucleic acid construct. Such embryos, fetuses, and animals are known in the art as being "transgenic." In certain embodiments, the large heterologous nucleic acid construct is an artificial chromosome, most preferably an ACEs or a euchromatin-based minichromosome.

The cells of the embryos, fetuses, and animals that comprise at least one artificial chromosome preferably comprise ten or fewer artificial chromosomes; more preferably comprise six or fewer artificial chromosomes, four or fewer artificial chromosomes, or two or fewer artificial chromosomes; and most preferably comprise one artificial chromosome. If the cells of the embryos, fetuses, and animals of the invention comprise more than one artificial chromosome, the artificial chromosomes may be identical or may differ from one another.

The term "transgenic" as used herein in reference to embryos, fetuses and animals refers to an embryo, fetus or animal comprising one or more cells that contain heterologous nucleic acids. In preferred embodiments, a transgenic embryo, fetus, or animal comprises one or more transgenic cells. While germ line transmission is not a requirement of transgenic embryos, fetuses, or animals as that term is used herein, in particularly preferred embodiments a transgenic embryo, fetus, or animal can pass its transgenic characteristic(s) through the germ line. In certain embodiments, a transgenic embryo, fetus or animal expresses one or more transgenes as transgenic RNA and protein molecules. Most preferably, a transgenic embryo, fetus or animal results from a nuclear transfer procedure using a transgenic nuclear donor cell.

Transgenic totipotent mammalian embryos can be established from cultured cybrids emanating from one or more nuclear transfer procedures, where one of the nuclear transfer procedures utilizes a totipotent mammalian cell harboring at least one artificial chromosome as a nuclear donor. A transgenic totipotent fetus can be established, for example, from a transgenic totipotent embryo that has been implanted into the uterus of a suitable female host. Cloned transgenic mammalian animals of the invention can be established from totipotent mammalian cells, totipotent mammalian embryos, and totipotent mammalian fetuses of the invention.

In certain embodiments, a transgenic animal embryo is produced by nuclear transfer of a nuclear donor cell into an enucleated recipient cell according to the following method: (a) a heterologous DNA molecule of greater than 100 kilobase pairs is introduced into one or more ungulate cells by microcell fusion; (b) the one or more cells are cultured to provide a cell culture; (c) a nuclear donor cell obtained from the cell culture is fused with an enucleated recipient cell to form a nuclear transfer embryo comprising the heterologous DNA molecule; and (d) the nuclear transfer embryo is activated to provide the transgenic ungulate embryo.

In particularly preferred embodiments, method further comprises one or more of the following: the culturing step comprises selection for one or more markers of said heterologous DNA molecule, whereby at least 90% of cells in said cell culture comprise the heterologous DNA molecule; the transgenic animal is an ungulate selected from the group consisting of a bovine, an ovine, a caprine, and a porcine; the heterologous DNA molecule comprises one or more telomeres, one or more centromeres, and one or more origins of replication; the heterologous DNA molecule is contained within the cells of the transgenic ungulate embryo on a replication unit that comprises essentially no homologous DNA; the activated nuclear transfer embryo is cultured to at least the two cell stage, wherein at least 50% of the cells of the transgenic ungulate embryo comprise the heterologous DNA molecule; the nuclear donor cell is selected from the group consisting of a somatic cell, a primordial germ cell, an embryonic germ cell, and an embryonic stem cell; the heterologous DNA molecule comprises a plurality of copies of at least one transgene; the heterologous DNA molecule is between 100 kilobase pairs and 500 megabase pairs in size; and the heterologous DNA molecule is an artificial chromosome.

In yet another aspect, the invention features a method of using a cloned transgenic fetus or animal, where one or more cells of the fetus or animal comprise one or more large heterologous nucleic acid constructs. The method of using a cloned transgenic fetus or animal comprises the step of isolating at least one component from the fetus or animal.

The term "component" as used herein can relate to any portion of a fetus or animal. A component can be selected from the group consisting of fluid, biological fluid, cell, tissue, organ, gamete, embryo, and fetus.

The term "gamete" as used herein refers to any cell participating, directly or indirectly, in the reproductive system of an animal. Examples of gametes are spermatocytes, spermatogonia, oocytes, and oogonia. Gametes can be present in fluids, tissues, and organs collected from animals (e.g., sperm is present in semen). For example, methods of collecting semen for the purposes of artificial insemination are well known to a person of ordinary skill in the art. See, e.g., *Physiology of Reproduction and Artificial Insemination of Cattle* (2nd edition), Salisbury et al., copyright 1961, 1978, WH Freeman & Co., San Francisco. However, the invention relates to the collection of any type of gamete from an animal.

The term "tissue" is defined previously. The term "organ" relates to any organ isolated from a fetus or animal, or any portion of an organ. Examples of organs and tissues are neuronal tissue, brain tissue, spleen, heart, lung, gallbladder, pancreas, testis, ovary, intestine, skin, and kidney. These examples are not limiting and the invention relates to any organ and any tissue isolated from a cloned animal of the invention.

In preferred embodiments, (1) fluids, biological fluids, cells, tissues, organs, gametes, embryos, and fetuses can be subject to manipulation; (2) the manipulation comprises isolating at least one component from an animal or fetus; (3) the manipulation comprises the step of cryopreserving the components; (4) the manipulation comprises the step of thawing components; (5) the manipulation comprises the step of separating the semen into X-chromosome bearing semen and Y-chromosome bearing semen; (6) the manipulation comprises methods of preparing the semen for artificial insemination; (7) the manipulation comprises the step of purification of desired polypeptide(s) from the component; (8) the manipulation comprises concentration of the components; and (9) the manipulation comprises the step of transferring one or more cloned cells, cloned tissues, cloned organs, and/or portions of cloned organs to a recipient organism (e.g., the recipient organism may be of a different species than the donor source).

The term "separating" as used herein in reference to separating semen refers to methods well known to a person skilled in the art for fractionating a semen sample into sex-specific fractions. This type of separation can be accomplished by using flow cytometers that are commercially available. Methods of utilizing flow cytometers from separating sperm by genetic content are well known in the art. In addition, semen can be separated by its sex-associated characteristics by other methods well known to a person of ordinary skill in the art. See, U.S. Pat. Nos. 5,439,362, 5,346,990, and 5,021,244, entitled "Sex-Associated Membrane Proteins and Methods for Increasing the Probability that Offspring Will Be of a Desired Sex," Spaulding, issued on Aug. 8, 1995, Sep. 13, 1994, and Jun. 4, 1991 respectively, all of which are incorporated herein by reference in their entireties including all figures, tables, and drawings.

Semen preparation methods are well known to someone of ordinary skill in the art. Examples of these preparative steps are described in *Physiology of Reproduction and Artificial Insemination of Cattle* (2nd. edition), Salisbury et al., copyright 1961, 1978, W.H. Freeman & Co., San Francisco.

The term "purification" as used herein refers to increasing the specific activity of a particular polypeptide or polypeptides in a sample. Specific activity can be expressed as the ratio between the activity of the target polypeptide and the concentration of total polypeptide in the sample. Activity can be catalytic activity and/or binding activity, for example. Alternatively, specific activity can be expressed as the ratio between the concentration of the target polypeptide and the concentration of total polypeptide. Purification methods include dialysis, centrifugation, and column chromatography techniques, which are well-known procedures to a person of ordinary skill in the art. See, e.g., Young et al., 1997, "Production of biopharmaceutical proteins in the milk of transgenic dairy animals," *BioPharm* 10(6): 34-38.

The term "transferring" as used herein can relate to shifting cells, tissues, organs, and/or portions of organs to an animal. The cells, tissues, organs, and/or portions of organs can be, for example, (a) developed in vitro and then transferred to an animal, (b) removed from an animal and transferred to another animal of a different specie, (c) removed from an animal and transferred to another animal of the same specie, (d) removed from one portion of an animal (e.g., the leg of an animal) and then transferred to another portion of the same animal (e.g., the brain of the animal), and/or (e) any combination of the foregoing. The term "transferring" can relate to adding cells, tissues, and/or organs to an animal and can also relate to removing cells, tissues, and/or organs from an animal and replacing them with cells, tissues, and/or organs from another source.

The term "transferring" as used herein can also refer to implanting one or more cells, tissues, organs, and/or portions of organs from the cloned mammalian animal into another organism. For example, neuronal tissue from a cloned mammalian organism can be grafted into an appropriate area in the human nervous system to treat neurological diseases such as Alzheimer's disease. Alternatively, cloned cells, tissues, and/or organs originating from a porcine organism may be transferred to a human recipient. Surgical methods for accomplishing this preferred aspect of the invention are well known to a person of ordinary skill in the art. Transferring procedures may include the step of removing or deleting cells, tissues, or organs from a recipient organism before a transfer step.

Of particular interest are transgenic animals that express genes that confer resistance or reduce susceptibility to disease. Since multiple genes can be introduced on an ACEs, a series of genes encoding an antigen can be introduced, which upon expression will serve to immunize [in a manner similar to a multivalent vaccine] the host animal against the diseases for which exposure to the antigens provide immunity or some protection.

Also of interest are transgenic animals that serve as models of certain diseases and disorders for use in studying the disease and developing therapeutic treatments and cures thereof. Such animal models of disease express genes [typically carrying a disease-associated mutation], which are introduced into the animal on a MAC, preferably an ACEs, and which induce the disease or disorder in the animal. Similarly, MACs carrying genes encoding antisense RNA may be introduced into animal cells to generate conditional "knock-out" transgenic animals. In such animals, expression of the antisense RNA results in decreased or complete elimination of the products of genes corresponding to the antisense RNA. Of further interest are transgenic mammals that harbor MAC-carried genes encoding therapeutic proteins that are expressed in the animal's milk. Transgenic animals for use in xenotransplantation, which express MAC-carried genes that serve to humanize the animal's organs, are also of interest. Genes that might be used in humanizing animal organs include those encoding human surface antigens.

The invention relates in part to any disease or parasitic condition known in the art. See, e.g., *Hagan &Bruners Infectious Diesases of Domestic Animals* (7th edition), Gillespie & Timoney, copyright 1981, Cornell University Press, Ithaca N.Y. Examples of parasites include, but are not limited to, worms, insects, invertebrate, bacterial, viral, and eukaryotic parasites. These parasites can lead to diseased states that can be controlled by the materials and methods of the invention.

The term "regulatory element" as used herein refers to a DNA or RNA sequence that can increase or decrease the amount of product produced from another DNA or RNA sequence. The regulatory element can cause the constitutive production of the product (e.g., the product can be expressed constantly). Alternatively, the regulatory element can enhance or diminish the production of a recombinant product in an inducible fashion (e.g., the product can be expressed in response to a specific signal). The regulatory element can be controlled, for example, by nutrition, by light, or by adding a substance to the transgenic organism's system. Examples of regulatory elements well-known to those of ordinary skill in the art are promoters, enhancers, insulators, and repressors. See, e.g., *Transgenic Animals, Generation and Use*, 1997, Edited by L. M. Houdebine, Hardwood Academic Publishers, Australia, hereby incorporated herein by reference in its entirety including all figures, tables, and drawings.

The terms "promoters," "promoter," or "promoter elements" as used herein refer to a DNA sequence that is located adjacent to a DNA sequence that encodes a recombinant product. A promoter is preferably operatively linked to the adjacent DNA sequence. A promoter typically increases the amount of recombinant product expressed from a DNA sequence as compared to the amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art. Examples of promoter elements are described hereafter.

The terms "enhancers," "enhancer" or "enhancer elements" as used herein refer to a DNA sequence that is located adjacent to the DNA sequence that encodes a recombinant product. Enhancer elements are typically located upstream of a promoter element or can be located downstream of the coding DNA sequence (e.g., the DNA sequence transcribed or translated into a recombinant product or products). Hence, an enhancer element can be located 100 base pairs, 200 base pairs, or 300 or more base pairs upstream of the DNA sequence that encodes the recombinant product. Enhancer elements can increase the amount of recombinant product expressed from a DNA sequence above the increased expression afforded by a promoter element. Multiple enhancer elements are readily available to persons of ordinary skill in the art.

The terms "insulators," "insulator," or "insulator elements" as used herein refer to DNA sequences that flank the DNA sequence encoding the recombinant product. Insulator elements can direct the recombinant product expression to specific tissues in an organism. Multiple insulator elements are well known to persons of ordinary skill in the art. See, e.g., Geyer, 1997, *Curr. Opin. Genet. Dev.* 7: 242-248, hereby incorporated herein by reference in its entirety, including all figures, tables, and drawings.

The terms "repressor" or "repressor element" as used herein refer to a DNA sequence located in proximity to the DNA sequence that encodes the recombinant product, where the repressor sequence can decrease the amount of recombinant product expressed from that DNA sequence. Repressor elements can be controlled by the binding of a specific molecule or specific molecules to the repressor element DNA sequence. These molecules can either activate or deactivate the repressor element. Multiple repressor elements are available to a person of ordinary skill in the art.

The terms "milk protein promoter," "urine protein promoter," "blood protein promoter," "tear duct protein promoter," "synovial protein promoter," "spermatogenesis protein promoter," and "mandibular gland protein promoter" refer to promoter elements that regulate the specific expression of proteins within the specified fluid or gland or cell type in an animal. For example, a milk protein promoter is a regulatory element that can control the expression of a protein that is expressed in the milk of an animal. Other promoters, such as β-casein promoter, melanocortin promoter, milk serum protein promoter, casein promoter, α-lactalbumin promoter, whey acid protein promoter, uroplakin promoter, and α-actin promoter, for example, are well known to a person of ordinary skill in the art.

The terms "insertion" and "introduction" as used herein in reference to artificial chromosomes or other large heterologous nucleic acid constructs refer to translocating one or more such artificial chromosomes or constructs from the outside of a cell to the inside of a cell. Insertion can be effected in at least two manners: by mechanical delivery and non-mechanical delivery.

The term "mechanical delivery" as used herein refers to processes that utilize an apparatus that directly or indirectly introduces DNA (e.g., one or more artificial chromosomes) into one or more cells. Examples of mechanical delivery of DNA into cells include, but are not limited to, microinjection, particle bombardment, sonoporation, and electroporation.

The term "non-mechanical delivery" as used herein refers to non-mechanical processes such as diffusive processes, for example. For instance, non-mechanical delivery may be effected by introducing DNA (e.g., an artificial chromosome) and one or more reagents to a medium bathing cell surfaces, where the reagents increase the probability that the DNA enters the cells. Such reagents are well known in the art, such as liposomes, acyl moieties, peptide moieties, saccharide moieties, and/or polyethylene glycol (PEG), for example. Such reagents may be complexed with the target molecule and the reagents may be introduced to cells in vivo and/or ex vivo. These examples are not meant to be limiting and the invention relates in part to any non-mechanical form of insertion.

The summary of the invention described above is not limiting and other features and advantages of the invention will be apparent from the following detailed description of the preferred embodiments, as well as from the claims.

DETAILED DESCRIPTION OF THE PREFERRED EMBODIMENTS

The invention relates in part to totipotent cells comprising at least one artificial chromosome. These cells can be utilized in nuclear transfer processes for establishing cloned transgenic embryos, fetuses, and animals. These cells and other materials and methods of the invention represent an improvement towards establishing cloned transgenic animals.

One improvement towards establishing cloned transgenic animals is that large units of target DNA (e.g., heterologous DNA) may be introduced to cells. Specifically, target DNA larger than 10 kb can be introduced into artificial chromosomes and these artificial chromosomes can be inserted into cells. Hence, genes and regulatory sequences larger than 10 kb in length can be inserted into one artificial chromosome and then introduced to cells; multiple types of regulatory sequences and multiple types of genes can be inserted into an artificial chromosome and then introduced to cells; and multiple copies of a given target DNA sequence can be incorporated into an artificial chromosome and then incorporated into a cell. These are examples of improvements and the invention also relates to other improvements.

In another improvement, the invention provides materials and methods that can provide in vitro control of in vivo recombinant product expression levels. Specifically, artificial chromosomes comprising a known copy number of a target DNA can be selected before the artificial chromosome comprising the target DNA is inserted into a cell of interest. The number of copies can be quantified by a variety of techniques known in the art, such as Southern blot and FISH procedures, for example. Hence, in contrast to techniques currently applied in the art for establishing cloned transgenic animals, expression levels of one or more recombinant products can be controlled by the number of copies of target DNA present in an artificial chromosome that encode these recombinant products.

Another improvement towards establishing cloned transgenic animals is that the location of target DNA within a transgenic cell can be controlled. Artificial chromosomes remain distinct and separate from endogenous genomic DNA (i.e., they exist as "extra-genomic" elements in the nucleus of the transgenic cell), thus providing a controlled and known locations of target DNA. This advantage is contrasted with many existing techniques for creating transgenic cells, which cause random insertion of target DNA into cell nuclear DNA. Because random insertion decreases efficiencies for establishing transgenic cells due to unproductive insertions that must be quantified in vivo, the materials and methods defined herein are improvements over the technology currently utilized in the art to clone transgenic animals.

The following descriptions define processes for establishing totipotent cells comprising one or more artificial chromosomes, introducing one or more artificial chromosomes into cells, and processes for utilizing totipotent cells that comprise one or more artificial chromosomes.

Establishing Totipotent Cells

The invention relates in part to establishing totipotent mammalian cells comprising one or more artificial chromosomes. These cells can be useful as nuclear donors in nuclear transfer procedures. Utilizing these cells in nuclear transfer procedures can improve the efficiency of processes for establishing cloned and transgenic embryos, fetuses, and animals.

Totipotent mammalian cells can be established from nearly any type of precursor cell. Examples of precursor cells are non-embryonic cells; non-fetal cells; differentiated cells; somatic cells; embryonic cells; fetal cells; embryonic stem cells; primordial germ cells; genital ridge cells; cells isolated from an asynchronous population of cells; and cells isolated from a synchronized population of cells where the synchronous population is not arrested in the $G_0$ stage of the cell cycle; and any of the forgoing that are cultured, cultured as cell lines, immortalized, and/or totipotent. These examples are not meant to be limiting and the invention relates to any precursor cell known in the art.

Processes for establishing totipotent cells having at least one artificial chromosome comprise one or more of the following procedures: (1) inserting at least one artificial chromosome into a cell; (2) introducing a stimulus to a cell; (3) conducting one or more nuclear transfer procedures, which may optionally include fusion and/or activation steps; and (4) selecting cells that comprise at least one artificial chromosome. These procedures can be conducted in any order and each procedure may be repeated more than once.

Materials and methods for introducing at least one artificial chromosome into a cell and selecting for cells that comprise an artificial chromosome are defined hereafter. Materials and methods for (1) culturing cells; (2) passaging and plating cells; (3) preparing and administering a stimulus to cells; (4) preparing feeder cells; (5) and (6) establishing totipotent cells, are defined in PCT application number WO 98/39416 entitled "Method of Cloning Animals," Strelchenko et al., filed Mar. 5, 1998, which is hereby incorporated herein by reference in its entirety including all figures, tables, and drawings.

Preparing Artificial Chromosomes

Artificial chromosome expression systems (ACes) containing multiple copies of several transgenes were incorporated into bovine embryos produced using nuclear transfer technologies. In the first approach, ACes were incorporated into bovine embryos by direct injection of ACes in enucleated oocytes just prior to their electrofusion with a nuclear donor cell to form a cybrid. Direct injection of ACes yield blastocysts in which up to 25% of the cells contained ACes.

In another approach, nuclear donor cells that contained ACes were enriched using hygromycin B and then used to generate nuclear transfer blastocysts that contain an artificial chromosome in 90% or more of cells for the purpose of producing cloned animals with specific traits or that express commercially relevant proteins in the mammary glands or other tissues.

The transfection of nuclear donor cells used in cloning has the distinct advantages of permitting the pre-selection of transgenic cells prior to nuclear transfer and providing for transgene incorporation in the majority of nucleated cells in the organism in the first generation. Because of the advantages of using transgenic nuclear donor cells, cloning has become the method of choice to generate transgenic animals. However, there are several limitations to current methods to produce transgenic nuclear donor cells. One limitation is that if the transgenes insert randomly into the genome, the expression of the transgene cannot be predicted. Position effects on transgene expression occur after all forms of gene delivery-microinjection, transfection, electroporation, infection, etc. In addition, random transgene integration is likely to cause mutations of critical genomic loci and generate a wide variety of abnormal phenotypes in cells and animals (Constantini et al., 1989; Rossant, 1991; Favor and Morawetz, 1992; Rijkers et al., 1994; Kurth, 1998; Woychik and Alagramam, 1998). If targeting to specific loci via homologous recombination is used, the size and copy number of the transgenes are limited.

In addition, introducing several different transgenes into the same locus simultaneously would likely prove difficult.

An approach to overcome the limitations of both random transgene insertion and transgene targeting is to introduce into nuclear transfer embryos an entirely new chromosome, ACes. The advantage of ACes is that instead of genes being inserted at random into the existing chromosomes of a cell or embryo, genes are engineered onto a separate chromosome with its own structure for extra-genomic maintenance and replication. ACes with specific transgenes of interest have been transmitted through the germline of mice following their injection into the pronuclei of zygotes (Coet al. 2000). In addition, these artificial chromosomes have been transferred into cells in vitro via microcell mediated chromosome transfer (Telenius et al. 1999) and other non-viral methods.

Artificial chromosomes are well known in the art. In particular, materials and methods for (1) preparing artificial chromosomes de novo, and (2) preparing recombinant vectors suitable for inserting heterologous DNA (e.g., heterologous with respect to artificial chromosome DNA and/or heterologous with respect to cell nuclear DNA) into an artificial chromosome are well known in the art. See, e.g., Kereso et al., 1996, *Chromosome Research* 4: 226-239, Holló et al., 1996, *Chromosome Research* 4: 240-247, U.S. Pat. No. 6,025,155, and U.S. Pat. No. 6,077,697.

Artificial chromosomes can comprise multiple elements, including (1) one or more repressor elements; (2) one or more insulator elements; (3) one or more promoter elements; (4) one or more enhancer elements; (5) one or more units of target DNA; (6) one or more units of neutral DNA; (7) a centromere; (8) one or more origins of replication; and (9) one or more telomeres. These elements are defined previously and are well known in the art. These elements are examples and the invention relates in part to other DNA elements known in the art. These elements can be repeated in any number in an artificial chromosome, and can be located in any order in an artificial chromosome. Repeated elements can be contiguous and/or non-contiguous. Related but different elements can also exist in an artificial chromosome. For example, an artificial chromosome may comprise one or more copies of target DNA that encodes one type of recombinant product and one or more copies of another type of target DNA that encodes another type of recombinant product.

Target DNA can encode recombinant products including, but not limited to, ribozymes; antisense RNA; peptides; polypeptides; proteins; structural proteins; antibodies; enzymes; and portions, fragments, mutants, deletions, and fusions of any of the foregoing. Examples of recombinant products encoded by target DNA include hormones, enzymes, growth factors, clotting factors, apolipoproteins, receptors, drugs, pharmaceuticals, bioceuticals, nutraceuticals, oncogenes, tumor antigens, tumor suppressors, cytokines, viral antigens, parasitic antigens, bacterial antigens and chemically synthesized polymers and polymers biosynthesized and/or modified by chemical, cellular and/or enzymatic processes. Specific examples of recombinant products include proinsulin, insulin, growth hormone, androgen receptors, casein, milk proteins, muscle proteins, insulin-like growth factor I, insulin-like growth factor II, insulin growth factor binding proteins, epidermal growth factor, TGF-$\alpha$, TGF-$\beta$, platelet-derived growth factor (PDGF), angiogenesis factors (acidic fibroblast growth factor, basic fibroblast growth factor, and angiogenin), matrix proteins (Type I collagen, Type IV collagen, Type VII collagen, laminin), oncogenes (ras, fos, myc, erb, src, sis, jun), E6 or E7 transforming sequence, p53 protein, cytokine receptor, IL-1, IL-6, IL-8, IL-2, $\alpha$, $\beta$, or $\gamma$IFN, GMCSF, GCSF, viral capsid protein, and proteins from viral, bacterial and parasitic organisms. Other specific proteins or polypeptides which can be expressed include: phenylalanine hydroxylase, $\alpha$-1-antitrypsin, cholesterol-7$\alpha$-hydroxylase, truncated apolipoprotein B, lipoprotein lipase, apolipoprotein E, apolipoprotein A1, LDL receptor, scavenger receptor for oxidized lipoproteins, molecular variants of each, VEGF, and combinations thereof. Other examples are clotting factors, fibrinogen, factor VIII, Von Willebrands Factor, $\alpha$-glucosidase, apolipoproteins, drugs, tumor antigens, viral antigens, parasitic antigens, monoclonal antibodies, and bacterial antigens. One skilled in the art readily appreciates that these proteins belong to a wide variety of classes of proteins, and that other proteins within these classes can also be used. These are only examples and are not meant to be limiting in any way.

It should also be noted that target DNA includes (1) nucleic acid sequences not normally found in the cells; (2) nucleic acid molecules which are normally found in the cells but not expressed at physiological significant levels; (3) nucleic acid sequences normally found in the cells and normally expressed at physiological desired levels; (4) other nucleic acid sequences which can be modified for expression in cells; and (5) any combination of the above.

Examples of promoter elements include, but are not limited to, milk protein promoter, urine protein promoter, blood protein promoter, tear duct protein promoter, synovial protein promoter, mandibular gland protein promoter, casein promoter, $\beta$-casein promoter, melanocortin promoter, milk serum protein promoter, $\alpha$-lactalbumin promoter, whey acid protein promoter, uroplakin promoter, and $\alpha$-actin promoter.

Materials and methods for manipulating DNA of mammalian cells are well-known to a person of ordinary skill in the art. See, e.g., Molecular Cloning, a Laboratory Manual, 2nd Ed., 1989, Sambrook, Fritsch, and Maniatis, Cold Spring Harbor Laboratory Press, hereby incorporated by reference in its entirety including all figures, tables, and drawings.

Introducing Artificial Chromosomes into Cells

Artificial chromosomes comprise DNA molecules that can be introduced into cells. Materials and methods for introducing DNA molecules into cells are well known in the art. The invention relates to introducing one or more artificial chromosomes into any type of cell. Examples of cell types are defined herein. Furthermore, artificial chromosomes can be introduced into cells when the cells are incorporated within fluids, tissues, organs, and animals.

DNA molecules can be introduced into cells by utilizing at least two types of processes. First, DNA can be inserted into cells by using mechanical processes, where DNA is physically inserted into a cell. Examples of mechanical processes are microinjection, sonoporation, electroporation, and particle bombardment. Second, DNA can be introduced into cells by using non-mechanical processes. Examples of diffusive processes known in the art are viral processes, non-viral processes, liposome-mediated cell fusion processes, peptide-mediated cell fusion processes, ligand/receptor processes, and diffusion processes that insert an entire complement of nuclear DNA into cells. The above-identified examples are not meant to be limiting and the invention relates to any combinations of materials and methods for introducing DNA into cells that are known in the art.

Materials and methods for DNA introduction processes are well known in the art. These methods include, but are not limited to, direct DNA transfer techniques, cell microinjection methods, micro particle bombardment processes, electroporation methods, cell fusion techniques, microcell fusion processes, lipid mediated transfer methods, lipofection processes, liposome mediated methods, protoplast regeneration processes, protoplast fusion methods, and polycation mediated techniques. See, e.g., Hogan et al., 1994, *Manipulating the Mouse Embryo, A Laboratory Manual*, Cold Spring Harbor Laboratory Press, Cold Spring Harbor, N.Y. (see especially pages 255-264 and Appendix 3); Liszewski, 1998, "Non-viral Strategies for Gene Therapy," *Genetic Engineering News* (Jan. 1, 1998): 13, 28, 32; Keown et al., 1990, *Methods in Enzymology* 185: 527-537; Mansour et al., 1988, *Nature* 336: 348-352; U.S. Pat. No. 5,491,075; U.S. Pat. No. 5,482,928; U.S. Pat. No. 5,424,409; U.S. Pat. No. 5,470,708; Kuo and Saltzman, 1996, "Novel Systems for Controlled Delivery of Macromolecules," *Critical Reviews in Eukaryotic Gene Expression* 6(1): 59-73; Monsigny et al., 1994, "Glycoconjugates as carriers for specific delivery of therapeutic drugs and genes," *Advanced Drug Delivery Reviews* 14: 1-24; Nicolau and Cudd, 1989, "Liposomes as Carriers of DNA," *Critical Review in Therapeutic Drug Carrier Systems* 6: 239-271; Papisov, 1995, "Modeling in vivo transfer of long-circulating polymers (two classes of long circulating polymers and factors affecting their transfer in vivo)," *Advanced Drug Delivery Reviews* 16: 127-139; Szoka and Papahadjopouls, 1980, "Comparative Properties and Methods of Preparation of Lipid Vesicles (Liposomes)," *Annual Reviews of Biophysics and Bioengineering* 9: 467-508; Gottschalk et al., 1996, "A novel DNA-peptide complex for efficient gene transfer and expression in mammalian cells," *Gene Therapy* 3: 448-457; Nicolau et al., 1987, "Liposomes as Carriers for in vivo Gene Transfer and Expression," *Methods in Enzymology* 149: 157-176; Simons et al., 1988, "Gene Transfer Into Sheep," *Bio/Technology* 6: 179-183; Yang, 1992, "Gene Transfer into Mammalian Somatic Cells in vivo," *Critical Reviews in Biotechnology* 12: 335-356; Behr, 1993, "Synthetic Gene-Transfer Vectors," *Acc. Chem. Res.* 26: 274-278; Davis et al., 1993, "Direct Gene Transfer into Skeletal Muscle in vivo: Factors Affecting Efficiency of Transfer and Stability of Expression," *Human Gene Therapy* 4: 151-159; Gao and Huang, 1995, "Cationic liposome-mediated gene transfer," *Gene Therapy* 2: 710-722; Rhodes et al., WO 93/14778 dated Aug. 5, 1993, PCT/US93/00492 dated Jan. 21, 1993, entitled "Ex Vivo Gene Transfer"; Wigler et al., 1978, "Biochemiical Transfer of Single-Copy Eucaryotic Genes Using Total Cellular DNA as Donor," *Cell* 14: 725-731; Yang et al., 1990, "In vivo and in vitro Gene Transfer to Mammalian Somatic Cells by Particle Bombardment," *Proc. Natl. Acad. Sci. USA* 87: 9568-9572; and Wagner et al., 1991, "DNA-Binding Transferrin Conjugates as Functional Gene-Delivery Agents: Synthesis by Linkage of Polylysine or Ethidium Homodimer to the Transferrin Carbohydrate Moiety," *Bioconjugate Chem.* 2: 226-231; Wigler et al., 1979, *Proc. Natl. Acad. Sci. USA* 76:1373-1376; Strauss, 1996, *Meth. Mol. Biol.* 54:307-327; Lambert, 1991, *Proc. Natl. Acad. Sci. USA* 88:5907-5911; U.S. Pat. No. 5,396,767, Sawford et al., *Somatic Cell Mol. Genet.* 13:279-284; Dhar et al., 1984, *Somatic Cell Mol. Genet.* 10:547-559; McNeill-Killary et al., 1995, *Meth. Enzymol.* 254:133-152; Teifel et al., 1995, *Biotechniques* 19:79-80; Albrecht et al., 1996, *Ann. Hematol.* 72:73-79; Holmen et al., 1995, *In Vitro Cell Dev. Biol. Anim.* 31:347-351; Remy et al., 1994, *Bioconjug. Chem.* 5:647-654; Le Bolch et al., 1995, *Tetrahedron Lett.* 36:6681-6684; Loeffler et al., 1993, *Methl. Enzynol.* 217:599-618; Teifel et al., 1995, *Biotechniques* 19:79-80; Albrecht et al., 1996, *Ann. Hematol.* 72:73-79; Holman et al., 1995, *In Vitro Cell Dev. Biol. Anim.* 31:347-351; Remy et al., 1994, *Bioconjug. Chem.* 5:647-654; Le Bolch et al., 1995, *Tetrahedron Lett.* 36:6681-6684; Loeffler et al., 1993, *Meth. Enzymol.* 217:599-618; Strauss, 1996, *Meth. Mol. Biol.* 54:307-327; Brazolot et al. 1991, *Mol. Repro. Dev.* 30:304-312; U.S. Pat. Nos. 4,955,378, 4,923,814, 4,476,004, 4,906,576 and 4,441,972; International PCT application publication No. WO 91/00358; U.S. Pat. Nos. 4,784,737, 5,501,967, 5,501,662, 5,019,034, 5,503,999; Fromm et al., 1985, *Proc. Natl. Acad. Sci. USA* 82:5824-5828; *Aq Biotechnology News* 7:3 and 17 September/October 1990; U.S. Pat. Nos. 5,240,840, 4,806,476, 5,298,429, 5,396,767; Fournier, 1981, *Proc. Nat. Acad. Sci. USA* 78:6349-6353; Lambert et al., 1991, *Proc. Natl. Acad. Sci. USA* 88:5907-59; Dieken et al., 1996, *Natura Genet.* 12:174-182, all of which are incorporated by reference herein in their entirety, including all figures, tables, and drawings.

For a cell that is to be used as a nuclear donor, one or more artificial chromosomes can be introduced into the cell prior to placing the cell into the perivitelline space of the recipient oocyte, or after placing the cell into the perivitelline space and just prior to fusion. In other embodiments, one or more artificial chromosomes can be introduced into the recipient oocyte prior to fusion with the nuclear donor cell. In yet other embodiments, one or more artificial chromosomes can be introduced into a pre-formed cybrid prepared by fusion of a nuclear donor cell with a recipient oocyte.

Additionally, in certain preferred embodiments, one or more artificial chromosomes are not introduced into the cell, but rather allowed to associate with the exterior of either the nuclear donor cell or the recipient oocyte. In these embodiments, the artificial chromosome can be carried into the cybrid at the time of fusion.

Cells comprising one or more artificial chromosomes can be selected against cells that do not comprise an artificial chromosome by identifying the artificial chromosome directly and by detecting a marker present in an artificial chromosome.

Methods for identifying an artificial chromosome directly are well known in the art. Examples of such methods include FISH (fluorescent in situ hybridization) and chromosome karyotyping, where the artificial chromosome can be detected in one cell by simply counting the number of chromosomes in the cell. An artificial chromosome is present in a cell if the cell has one or more chromosomes in addition to the number of chromosomes normally present in such a cell. One cell that contains one or more artificial chromosomes can be utilized to establish a cell culture of such cells.

Markers are well known in the art. Examples of markers are drug resistance genes, such as genes that render a cell resistant to such drugs as neomycin, hygromycin, blasticidin S, and puromycin. These examples are not meant to be limiting. Other examples of markers are genes that express enzymes that directly or indirectly modify substrates, such as a gene which encodes β-galactosidase and a gene that encodes luciferase. If an artificial chromosome harbors more than one marker, multiple markers can be identified. Similarly, if a cell comprises more than one artificial chromosome, where each artificial chromosome harbors a distinct marker, multiple markers may be identified. Materials and methods for conducting such selection processes are well known in the art. Examples of processes for detecting markers in cells are polymerase chain reaction and FISH procedures by utilizing appropriate DNA probes. Hence, identifying cells comprising one or more artificial chromosomes can be accomplished by utilizing materials and methods well known in the art.

Processes that Utilize Totipotent Cells Comprising Artificial Chromosomes

The invention relates in part to processes that utilize totipotent cells comprising artificial chromosomes. These cells are preferably utilized as nuclear donors in nuclear transfer processes, where the nuclear donor is inserted into a recipient oocyte. Nuclear transfer procedures typically include a translocation step, where the nuclear donor is inserted into a recipient oocyte. Nuclear transfer procedures can optionally include a fusion step (e.g., effected by one or more electric pulses and/or one or more fusion agents) and can optionally include an activation step (e.g., electrostimulation and/or ionomycin coupled with DMAP). Nuclear transfer processes may include one or more nuclear transfer cycles and the various steps in each cycle can be executed in any order and may be repeated more than once in any cycle.

Nuclear transfer processes can give rise to cloned embryos, where the embryonic cells comprise one or more artificial chromosomes. One or more nuclear transfer cycles may be utilized to establish cloned embryos, fetuses, and animals of the invention. These cloned embryos can develop into a cloned fetus where the fetal cells comprise one or more artificial chromosomes. Cloned fetuses may be established, for example, when cloned transgenic embryos are implanted into an uterus of a suitable recipient female. Cloned transgenic animals may be established when cloned transgenic fetuses are allowed to develop into an animal.

Cells isolated from cloned embryos, fetuses, and animals can be subjected to selection processes defined previously to determine whether the cells comprise one or more artificial chromosomes. In addition, entire embryos and fetuses may be subjected to these selection processes.

Cells obtained from fetuses, embryos, and animals produced by the nuclear transfer procedures described herein can be used in a second nuclear transfer, or recloning, procedure. For example, blastomeres from a first nuclear transfer embryo can be used as nuclear donors, or used to establish a cell line, which cells are used as nuclear donors. Alternatively, a fetus can be harvested from a maternal host, and one or more cells used directly as nuclear donors, or used to establish a cell line, which cells are used as nuclear donors. Such cells can undergo selection for the presence of an artificial chromosome, as described herein. In addition, cells obtained from a transgenic animal can be used directly as nuclear donors, or used to establish a nuclear donor cell line.

Materials and methods for (1) conducting one or more nuclear transfer cycles; (2) conducting nuclear donor insertion processes; (3) conducting fusion processes; (4) conducting activation processes; (5) preparing oocytes as nuclear recipients; (6) preparing totipotent cells as nuclear donors; (7) culturing embryos; (8) manipulating embryos; (9) implanting one or more embryos into an uterus of an appropriate animal; (10) manipulating fetuses; and (11) using cloned animals, are defined in PCT application entitled "Method of Cloning Animals," Strelchenko et al., filed Mar. 5, 1998.

EXAMPLES

The examples below are non-limiting and are merely representative of various aspects and features of the present invention.

Example 1

Incorporating Artificial Chromosomes Into Cells

The present invention describes methods to incorporate artificial chromosomes into the nuclei of bovine embryos. One of these methods, using microcell mediated chromosome transfer into nuclear transfer donor cells, has yielded bovine blastocysts where greater than 90% of the cells contain one ACes/cell. Another method where ACes were injected into enucleated oocytes prior to fusion with a nuclear transfer donor cell has produced blastocysts where up to 25% of the cells contain one ACes/cell. The potential advantage of injecting ACes into enucleated oocytes is that transgenic embryos could be generated more quickly since the microcell fusion and selection processes would be avoided.

The combination of ACes and nuclear transfer technologies, as described herein, makes possible the generation of transgenic embryos containing one or more artificial chromosomes in a majority of cells. ACes are ideal chromosome vectors, they can be engineered with large payloads (Mb), isolated, delivered, and maintained as discrete non-integrating chomosomes for long-term stability in animals, and they eliminate the concerns of insertional mutagenesis. Another useful feature is that transgene expression from ACes can be evaluated in cell lines and mice prior to generating transgenic animals.

Generation of β-ACes.

The formation of the satellite DNA-based artificial chromosome has been described previously (Kereso, et al. 1996). The murine ACes described therein contained approximately 60 million base pairs (Mb) of DNA and included centromere, telomeres, blocks of murine satellite repeats, and two regions of heterologous DNA, including five copies of the lacZ gene encoding β-galactosidase and six copies of the hygromycin phosphotransferase gene which conferred hygromycin resistance ("β-ACes").

Generation of Embryonic Germ (EG) Cells.

Genital ridge cells from bovine fetuses of age 50-60 days were isolated as follows. The genital ridges from a fetus were minced in 2 ml of TL-HEPES (Bio Whittaker #04-616F) containing 3 mg/ml protease (Sigma #p6911) using sterile surgical blades. The minced genital ridges were incubated at 37° C. for 40-50 minutes, and then disaggregated by tituration with a 2 ml syringe and 25 gauge needle. The disaggregated genital ridge cell suspension was combined with 10 ml of TL-HEPES in a 15 ml sterile tube and centrifuged at 300×g for 10 min. After aspiration of the supernatant, the disaggregated cells were resuspended in 10 ml of α-MEM medium (Gibco #32571-037) plus 10% FBS (Hyclone #A-111-D), and 0.1 mM β-mercaptoethanol. The resuspended cells were divided evenly between ten culture flasks (75 cm$^2$) containing mitotically inactivated fetal mouse feeder cells and culture with α-MEM medium (10 ml) supplemented with 25 ng/ml each of bovine basic fibroblast growth factor (bFGF) and human recombinant leukemia inhibitory factor (hrLIF).

After 7-10 days in culture, the culture flasks had become confluent with small, densely packed cells referred to as embryonic germ ("EG") cells. The EG cells were passaged into 25 culture dishes (5×10$^6$ cells/10 cm dish) containing 7 ml of α-MEM medium for the microcell fusion procedure.

Microcell Transfer of β-ACes to EG Cells.

Microcells carrying β-ACes were produced from the rodent/hybrid cell line mM2C1 and transferred to bovine EG cells as described before (Telenius et al., 1999) with minor modifications. 142×10$^6$ metaphase cells were loaded on five 50% Percoll (Pharmacia) cushions, generating 660×10$^6$ microcells. 540×10$^6$ microcells were fused to 1.25×10$^8$ recipient EG cells. Fusion was performed with 37% PEG 1450 (Sigma) for 3 minutes at 37° C., followed by drug-selection in 0.125 mg/ml hygromycin-B (Calbiochem) beginning 18-24 hours post-fusion. The duration of drug selection was 10-14 days. Hygromycin resistant cells were used for nuclear transfer 14-30 days following initiation of drug selection.

Example 2

Nuclear Transfer

Nuclear transfer of hygromycin-resistant EG cells was performed as described above (and in Strelchenko et al. 2000). Enucleated oocyte-donor cell complexes were fused by electroporation, activated chemically, and cultured for 7-10 days.

Isolation of ACes

β-ACes were isolated and purified by flow cytometry according to de Jong et al. (1999) except for the modification of the sheath buffer (10 mM Tris-HCl pH 7.5, 0.1 mM EDTA, 100 mM NaCl, 30 μM spermine, and 70 μM spermidine) (J-buffer). Just prior to use, the β-ACes were concentrated by centrifugation at 2500×g for 15 min at 4° C. in a swinging bucket rotor. All but 50 μl of the supernatant was removed and the pellet was resuspended by gently tapping the tube.

Microinjection of β-ACes into Cybrids Prior to Fusion

Enucleated oocytes with the donor cell in position under the zona pellucida (enucleated oocyte-donor cell complexes) were placed in a 25 μl drop of TL-HEPES medium on a 10 cm petri dish. 10-20 μl of concentrated β-ACes were placed in a separate drop of J-Buffer (25 μl). The drops were then covered with mineral oil.

A single ACes was drawn into a microinjection needle (Humagen # MIC-10,7 μm O.D.) and the needle was pressed against the oocyte plasma membrane adjacent to the nuclear donor cell. With controlled negative pressure, the membrane was drawn into the needle until the oocyte membrane ruptured. The cytoplasm drawn into the needle by this process was gently expelled back into the oocyte with the β-ACes such that the single β-ACes were placed adjacent to the nuclear donor cell.

The ACes-containing oocyte was then fused with the donor cell by electroporation using standard procedures (Strelchenko et al., 2000). The resulting embryos were activated and cultured for 7-10 days as described previously (Strelchenko et al., 2000).

Microinjection of β-ACes into Cybrids Subsequent to Fusion

After fusion of a nuclear donor cell with an enucleated oocyte, as described herein, the resulting cybrid is placed in a drop of TL-HEPES under mineral oil on a 10 cm petri dish. 10 to 20 μL of concentrated β-ACes are placed in a separate drop of J-Buffer. A single β-ACes is drawn into a microinjection needle (Humagen # MIC-10,7 μm O.D.) and the needle is pressed against the cybrid plasma membrane, preferably near the donor cell nucleus. With controlled negative pressure, the cybrid membrane is drawn into the needle until the oocyte membrane ruptures. The cytoplasm drawn into the pipet by this process is gently expelled back into the oocyte with the β-ACes such that the single β-ACes is placed adjacent to the donor cell nucleus.

Fluorescent In Situ Hybridization (FISH)

Metaphase preps of 7 to 10 day old expanded blastocysts were prepared by growing them for 12 hours in medium containing 1 μg/ml colchicine. The blastocyst was placed on a slide in 30 μl of 2:1 dH$_2$O:medium for 5 minutes. As much liquid as possible was removed and 30 μl of 0.01 M HCl/0.1% Tween-20 was added to the embryo until the zona pellucida dissolved and the cells started to disaggregate. A drop of cold fixative (3:1 methanol:acetic acid) was dropped onto the cells. The slide was allowed to dry and age at least 24 hours before proceeding with FISH. Extended embryo cultures were generated by culturing blastocysts in medium in 25 cm$^2$ culture flasks and were prepared for FISH in the same manner as the blastocysts with the exception that a portion of the attached cultures were dislodged from the tissue flask using an 18 gauge needle and a 1 ml pipet.

All general DNA manipulations were performed by standard procedures (See, e.g., Molecular Cloning, a Laboratory Manual, 2nd Ed., 1989, Sambrook, Fritsch, and Maniatis, Cold Spring Harbor Laboratory Press). Genomic DNA was prepared from bovine EG cells using the Wizard genomic kit (Promega). Primers 5'-ATCCAGACAGACAAGACAAGA-CAT-3' and 5'-TTCCAGCGAGCGGCAAGGAC-3' were used to amplify a 1.9 Kb fragment from bovine satellite 1.709 (Accession No. X00979; Skowronski et al., 1984). PCR amplification conditions were as follows: 25 cycles at 90° C. for 30 sec., 50° C. for 30 sec., 72° C. for 120 sec. The PCR product was purified and digested with EcoRI and subcloned into the plasmid vector Bluescript SK (Stratagene), generating plasmid pBSAT-1.709. A biotinylated bovine satellite 1.709 DNA probe was prepared from pBSAT-1.709 DNA using the Biotin-Nick Translation Mix (Boehringer Mannheim). Digoxigenin labeled mouse major satellite DNA probe was prepared from plasmid pSAT-2 (Wong and Rattner, 1988) using the DIG-Nick Translation Mix Boehringer Mannheim). FISH was performed as previously described (Pinkel et al., 1986). Bovine satellite probe does not cross hybridize to murine or hamster DNA sequences; the mouse major satellite probe does not cross hybridize with bovine DNA sequences.

Microcell Transfer

Two microcell transfer experiments resulted in successful generation of hygromycin-B resistant (hyg$^R$) EG cell colonies (>65). Hyg$^R$-EG cells were used as nuclear donor cells in nuclear transfer and 33 blastocysts were generated from 136 cybrids (24%). Expanded blastocysts (21) were placed in extended embryo culture to generate a cell line. Two of these embryo cell lines were proliferated to a point where FISH analysis could be performed. One embryo cell line comprised 1 β-ACes/cell in greater than 90% of the cells while the other cell line comprised 2 β-ACes/cell in greater than 90% of the cells.

The method of introducing β-ACes via microcell fusion has the advantage of producing blastocysts with little or no mosaicism. Since transgenic EG cells which have survived a similar selection regime as those described herein has produced live calves (Strelchenko et al., 2000), β-ACes-containing EG cells can be expected to be successful as nuclear donors for cloning bovines.

Injection of ACes into Enucleated Oocyte-Donor Cell Complexes

β-ACes were injected into 140 enucleated oocyte-donor cell complexes and the resulting enucleated oocyte-donor cell complexes were fused, activated and cultured as described elsewhere. β-ACes-injected cybrids developed at similar frequencies (39%) as the noninjected cybrids. Twenty-eight blastocysts were analyzed by FISH, of which 12 (43%) blastocysts contained β-ACes. Mosaicism in the transgenic blastocysts ranged from 1-25% (1 at 25%, 1 at 10%, 4 at 2%, and 6 at 1%).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents, patent applications, and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of neomycin, hygromycin, and puromycin, claims for X being neomycin and claims for X being hygromycin and puromycin are fully described.

Other embodiments are set forth within the following claims.

We claim:

1. A method of producing a transgenic ungulate embryo comprising one or more cells, wherein at least 90% of said one or more cells comprise a human chromosome fragment of greater than 100 kilobase pairs, by transfer of a nuclear donor cell into an enucleated ungulate recipient oocyte, the method comprising:
   (a) fusing a nuclear donor cell, or a nucleus thereof, with an enucleated ungulate recipient oocyte to form a transgenic ungulate embryo, wherein a human chromosome fragment of greater than 100 kilobase pairs is introduced into said nuclear donor cell or oocyte prior to or following said fusing, whereby said transgenic ungulate embryo comprises said human chromosome fragment; and
   (b) activating said transgenic ungulate embryo to yield an embryo comprising one or more cells, wherein at least 90% of the one or more cells comprise said human chromosome fragment.

2. The method according to claim 1, wherein the transgenic ungulate embryo is selected from the group consisting of a bovine, an ovine, a caprine, and a porcine.

3. The method according to claim 1, wherein the human chromosome fragment comprises one or more telomeres, one or more centromeres, and one or more origins of replication.

4. The method according to claim 1, wherein the human chromosome fragment comprises essentially no homologous DNA.

5. The method according to claim 1, wherein said transgenic ungulate embryo is cultured to at least the two cell stage, wherein at least 90% of the cells of the transgenic ungulate embryo comprise the human chromosome fragment.

6. The method according to claim 1, wherein the nuclear donor cell is selected from the group consisting of a somatic cell, a primordial germ cell, an embryonic germ cell, and an embryonic stem cell.

7. The method according to claim 1, wherein said human chromosome fragment is between 100 kilobase pairs and 500 megabase pairs.

8. A method of producing a transgenic ungulate from a transgenic ungulate embryo of claim 1, wherein at least 90% of the cells making up said ungulate comprise a human chromosome fragment of greater than 100 kilobase pairs, the method comprising: transferring said transgenic ungulate embryo into a maternal ungulate host so as to produce a fetus of full fetal development and parturition to generate said transgenic ungulate.

9. The method according to claim 8, wherein prior to said transferring step, said transgenic ungulate embryo is cultured to at least the two cell stage.

10. A method of producing a transgenic ungulate from a transgenic ungulate embryo of claim 1, wherein at least 90% of the cells making up said ungulate comprise a human chromosome fragment of greater than 100 kilobase pairs, the method comprising:
    (a) transferring said transgenic ungulate embryo into a maternal ungulate host so as to produce a fetus;
    (b) obtaining a nuclear donor cell from said fetus, wherein said cell comprises said human chromosome fragment;
    (c) fusing said nuclear donor cell, or a nucleus thereof, with an enucleated ungulate recipient oocyte to form a second transgenic ungulate embryo, wherein said second transgenic ungulate embryo comprises said human chromosome fragment;
    (d) activating said second transgenic ungulate embryo; and
    (e) transferring said second transgenic ungulate embryo into a maternal ungulate host so as to produce a fetus of full fetal development and parturition to generate said transgenic ungulate.

11. The method according to claim 10, wherein prior to said transferring step, said transgenic ungulate embryo and/or said second transgenic ungulate embryo is cultured to at least the two cell stage.

12. A method of producing a transgenic ungulate from a transgenic ungulate embryo of claim 1, wherein at least 90% of the cells making up said ungulate comprise a human chromosome fragment of greater than 100 kilobase pairs, the method comprising:
    (a) transferring said transgenic ungulate embryo into a maternal ungulate host so as to produce a fetus;
    (b) obtaining one or more cells from said fetus, wherein one or more of said cells comprise said human chromosome fragment, and culturing said one or more cells to obtain a cell culture;
    (c) fusing a nuclear donor cell obtained from said cell culture, or a nucleus thereof, with an enucleated ungulate recipient oocyte to form a second transgenic ungulate embryo, wherein said second transgenic ungulate embryo comprises said human chromosome fragment;

(d) activating said second transgenic ungulate embryo; and (e) transferring said second transgenic ungulate embryo into a maternal ungulate host so as to produce a fetus of full fetal development and parturition to generate said transgenic ungulate.

13. The method according to claim 12, wherein prior to said transferring step, said transgenic ungulate embryo and/or said second transgenic ungulate embryo is cultured to at least the two cell stage.

14. The method according to claim 12, wherein at least 90% of cells in said cell culture comprise said human chromosome fragment.

15. A transgenic ungulate embryo comprising one or more cells, wherein at least 90% of said one or more cells comprise a human chromosome fragment, wherein said human chromosome fragment comprises at least 1 megabase pairs.

16. A transgenic ungulate, wherein at least 90% of the cells making up said ungulate comprise a human chromosome fragment, wherein said human chromosome fragment comprises at least 1 megabase pairs.

17. The method of claim 1, wherein said transgenic ungulate embryo is a blastocyst.

18. The method according to claim 1, 8, 10, or 12, wherein the human chromosome fragment comprises at least 1 megabase pairs.

19. The method according to claim 18, wherein the human chromosome fragment comprises between 1 megabase pairs and 500 megabase pairs.

20. The transgenic ungulate embryo of claim 15, wherein said transgenic ungulate embryo is a transgenic ungulate blastocyst.

21. The transgenic ungulate embryo of claim 15, wherein said human chromosome fragment comprises between 1 megabase pairs and 500 megabase pairs.

22. The transgenic ungulate of claim 16, wherein said human chromosome fragment comprises between 1 megabase pairs and 500 megabase pairs.

23. A transgenic ungulate embryo comprising one or more cells, wherein at least 90% of said one or more cells comprise a human chromosome fragment.

24. The transgenic ungulate embryo of claim 23, wherein said transgenic ungulate embryo is a transgenic ungulate blastocyst.

25. A transgenic ungulate, wherein at least 90% of the cells making up said ungulate comprise a human chromosome fragment.

* * * * *

UNITED STATES PATENT AND TRADEMARK OFFICE
CERTIFICATE OF CORRECTION

| | | |
|---|---|---|
| PATENT NO. | : 7,652,192 B2 | Page 1 of 1 |
| APPLICATION NO. | : 10/468951 | |
| DATED | : January 26, 2010 | |
| INVENTOR(S) | : Forsberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1107 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,652,192 B2 | |
| APPLICATION NO. | : 10/468951 | |
| DATED | : January 26, 2010 | |
| INVENTOR(S) | : Forsberg et al. | |

It is certified that error appears in the above-identified patent and that said Letters Patent is hereby corrected as shown below:

Title page, Item (54) and Col. 1, Line 1, replace "UNGLULATES" with --UNGULATES--.

Column 2, Line 52, replace "ant" with --any--.

Column 4, Line 61, replace "chromsomes" with --chromosomes--.

Column 16, Line 60, replace "oocyte" with --oocyte.--.

Column 17, Line 37, replace "specie" with --species--.

Column 26, Line 31, replace "specie" with --species--.

Line 32, replace "specie" with --species--.

Column 27, Line 16, replace "*Diesases*" with --*Diseases*--.

Column 33, Line 41, replace "Biochemiical" with --Biochemical--.

Line 60, replace "*Methl. Enzynol*" with --*Meth. Enzymol*--.

Signed and Sealed this
Nineteenth Day of July, 2011

David J. Kappos
*Director of the United States Patent and Trademark Office*